(12) United States Patent
Toback et al.

(10) Patent No.: US 6,482,934 B1
(45) Date of Patent: Nov. 19, 2002

(54) METHODS AND COMPOSITIONS FOR DETECTING AND TREATING KIDNEY DISEASES ASSOCIATED WITH ADHESION OF CRYSTALS TO KIDNEY CELLS

(75) Inventors: F. Gary Toback, Chicago, IL (US); John C. Lieske, Rochester, MN (US)

(73) Assignee: ARCH Development Corp., Chicago, IL (US)

( * ) Notice: Subject to any disclaimer, the term of this patent is extended or adjusted under 35 U.S.C. 154(b) by 0 days.

(21) Appl. No.: 09/537,226

(22) Filed: Mar. 28, 2000

Related U.S. Application Data

(63) Continuation-in-part of application No. 08/837,226, filed on Apr. 10, 1997, now Pat. No. 6,043,216, which is a continuation-in-part of application No. 08/389,005, filed on Feb. 15, 1995, now Pat. No. 5,618,917.

(51) Int. Cl.$^7$ ............................................... C07H 21/02
(52) U.S. Cl. ..................... 536/23.1; 536/23.1; 530/300; 530/350; 435/6; 435/69.1; 435/7.1; 435/320.1; 514/2; 514/8; 514/21
(58) Field of Search .......................... 536/23.1; 435/6, 435/69.1, 7.1, 320.1; 530/350, 300; 514/8, 2, 21

(56) References Cited

PUBLICATIONS

Aithal, et al., (1988) "An alternate method utilizing small quantities of ligand for affinity purification of monospecific antibodies," *J. Immunol. Meth.* 112:63–70.
Aithal, et al., (1994) "Glyceraldehyde–3–phosphate dehydrogenase modifier protein is associated with microtubules in kidney epithelia cells," *Am. J. Physiol.* 266:F612–619.
Bitter, et al., (1962) "A modified uronic acid carbazole reaction," *Anal. Biochem.* 4:330–334.
Carey, et al., (1989) "Membrane anchoring of heparan sulfate proteoglycans by phosphatidylinositol and kinetics of synthesis of peripheral and detergent–solubilized proteoglycans in Schwann cells," *J. Cell. Biol.* 198:1891–1897.
Fernandez, et al. (1994) "An improved procedure of enzymatic digestion of polyvinylidene difluoride–bound proteins for internal sequence analysis," *Anal. Biochem.* 218:112–117.
Ginsburg, et al. (1986) "cDAN cloning of human plasminogen activator–inhibitor from endothelial cells," *J. Clin. Invest.* 78:1673–1680.
Grotendorst, G.R. (1984) "Alteration of the chemotactic response of NIH/3T3 cells to PDGF by growth factors, transformation, and tumor promoters," *Cell* 36:279–285.
Hess, B. (1992) "Tamm–Horsfall glycoprotein—Inhibitor of promoter of calcium oxalate monohydrate crystallization processes," *Urol. Res.* 20:83–86.
Hess, et al. (1989) "Inhibition of calcium oxalate monohydrate crystal aggregation by urine proteins," *Am. J. Physiol.* 257:F99–F106.
Kakehi, et al. (1996) "Analysis of glycoproteins, glycopeptides and glycoprotein–derived oligosaccharides by high–performance capillary electrophoresis," *J. Chromatog. A* 720:377–393.
Lieske, et al. (1994) "Renal epithelial cells rapidly bind and internalize calcium oxalate monohydrate crystals," *Proc. Natl. Acad. Sci. USA* 91:6987–6991.
Lieske, et al. (1993) "Regulation of renal epithelial cell endocytosis of calcuim oxalate monohydrate crystals," *Am. J. Physiol.* 264: F800–F807.
Lieske, et al. (1992) "Calcium oxalate monohydrate crystals are endocytosed by renal epithelial cells and induce proliferation," *Am. J. Physiol.* 262 (Renal *Fluid Electrolyte Physiol.* 31): F622–F630.
Lieske, et al. (1992) "Endocytosis of calcium oxalate crystals and proliferation of renal tubular epithelial cells in a patient with type 1 primary hyperoxaluria," *J. Urol.* 148:1517–1519.
Linker, et al. (1972) "Heparinase and heparitinase from flavobacteria," *Meth. Enzymol.* 28:902–911.
Nakagawa, et al. (1983) "Purification and characterization of the principal inhibitor of calcium oxalate monohyrate crystal growth in human urine," *J. Biol. Chem.* 258:12594–12600.
Nakagawa, et al. (1981) "Purification and characterization of a calcium oxalate monohydrate crystal growth inhibitor from human kidney tissue culture medium," *J. Biol. Chem.* 256:3936–3944.
Paulus, et al. (1996) "Detection of carbohydrates in capillary electrophoresis," *J. Chromatog. A* 720:353–376.
Porile, et al. (1996) "Normal calcium oxalate crystal growth inhibition in severe calcium oxalate nephrolithiasis," *J. Am Soc Nephrol* 7:602–607.
Posnett, et al. (1988) "A novel method for producing anti–peptide antibodies," *J. Biol. Chem.* 263:1719–1725.
Sukhatme, et al. (1987) "A novel early growth response gene rapidly induced by fibroblast, ephithelial cell and lymphocyte mitogens," *Oncogene Res* 1:343–355.
Tartof, et al. (1988) "New cloning vectors and techniques for easy and rapid restriction mapping," *Gene* 67:169–182.
Toback F.G. (1980) "Induction of growth in kidney epithelial cells in culture by Na+," *Proc. Natl. Acad. Sci. USA* 77:6654–6656.

(List continued on next page.)

*Primary Examiner*—Karen Cochrane Carlson
*Assistant Examiner*—Hope A. Robinson
(74) *Attorney, Agent, or Firm*—Barnes & Thornburg; Alice O. Martin

(57) ABSTRACT

An autocrine crystal adhesion inhibitor called CAI is an anionic, sialic acid-containing glycoprotein secreted by kidney epithelial cells that blocks adhesion of calcium oxalate monohydrate (COM) crystals to the cell surfaces. Novel amino acid sequences are shown for the amino-acid terminus and 6 interval fragments. Persons may be classified according to risk of developing kidney stones, by measuring the amount of CAI in a biological sample. Treatment efficacy is also monitored by this method. CAI is administered in vivo to prevent nephrolithiasis. A rapid, simple assay to detect agents that inhibit adhesion of COM crystals to the surface of kidney epithelial cells is characterized.

1 Claim, 6 Drawing Sheets

OTHER PUBLICATIONS

Vorbrodt A.W. (1989) "Ultracytochemical characterization of anionic sites in the wall of brain capillaries," *J. Neurocytol.* 18:359–368.

Walsh–Reitz, et al. (1983) "Kidney epithelial cell growth is stimulated by lowering extracellular potassium concentration," *Am. J. Physiol.* 244 (Cell *Physiol.* 13):C429–C432.

Walsh–Reitz, et al. (1986) "Lowering extracellular Na+ concentration release autocrine growth factors from renal epithelia cells," *Procl. Natl. Acad. Sci. USA* 83:4764–4768.

Yamagata, et al. (1968) "Purificaiton and properties of bacterial chondroitinases and chondrosulfatases," *J. Biol. Chem.* 243:1523–1535.

Amino Acid Sequence of CAI Fragments

| Fragment | Amino Acid |
|---|---|
| NH$_2$-terminal | (K/D) I N G G G A T L P Q P L Y Q T S G V L T A G F A P Y I (S) V (N) (A) (K)<br>(SEQ ID NO:4) |
| 1 | (F) V V T T N F A D S F G V P A G A V P A V T S Q G V M D (S/A) (L) (N)<br>(SEQ ID NO:20) |
| 2 | L I Q V P S V A T S V A I P F N K<br>(SEQ ID NO:6) |
| 3 | L A F L N N D Y S Q F G T G T K<br>(SEQ ID NO:21) |
| 4 | A A I T S N F V T A T S A L<br>(SEQ ID NO:22) |
| 5 | L T S T E L S T Y A S T K<br>(SEQ ID NO:8) |
| 6 | N R F V P L P T A X (K)<br>(SEQ ID NO:23) |

Fig. 6

Homology of the Amino-Terminal Fragment of CAI to Other Proteins

| CAI: | DINGGGATLPQPLYQTSGVL (SEQ ID NO:17) |
|---|---|
| | D+    GGATLPQPLYQT+GVL |
| Periplasmic [Fe]-hydrogenase: | DVVPGGATLPQPLYQTAGVL (SEQ ID NO:18) |

| CAI: | DINGGGATLPQPLY |
|---|---|
| | GGGATLP+   LY |
| Urinary tract stone matrix protein: | AVVGGGATLPEKLY (SEQ ID NO:19) |

+ refers to a conservative substitution.

Fig. 7

METHODS AND COMPOSITIONS FOR DETECTING AND TREATING KIDNEY DISEASES ASSOCIATED WITH ADHESION OF CRYSTALS TO KIDNEY CELLS

The present application claims priority from continuation-in-part of U.S. Ser. No. 08/389,005 filed Feb. 15, 1995 and issued as U.S. Pat. No. 5,618,917 on Apr. 8, 1997, and a continuation-in-part of U.S. Ser. No. 08/837,226 issued as U.S. Pat. No. 6,043,216 on Mar. 28, 2000.

The U.S. government may have rights in the present invention because of National Institutes of Health National Research Service Award DK-08618; Clinical Investigator Award K08 DK-02272 to J. C. Lieske; National Institutes of Health National Research Service Award F32 DK 08618 to J. C. Lieske; grants R01 DK 39689, R01 18413, R01 DK 37227, P01 DK 33949, p50 dk 47631 Digestive Diseases Center Grant DK-42086, and Cancer Research Center Grant CA-14599

An inhibitor is described that prevents adhesion of specific crystals to the surface of kidney cells and is used in an assay system to rapidly measure relative amounts of crystal adhesion to cells. Uses of the inhibitor include preventing kidney stone disease, identifying individuals at high risk of kidney disease, and screening for drugs which prevent adhesion of crystals to cells.

Kidney diseases are major public health problems. At least 3,000,000 people in the United States are affected annually. A type of kidney disease is the formation of "stones," a process called nephrolithiasis. An estimated 1% of adult males in industrialized countries have "stones."

Although nephrolithiasis is a common disease, the mechanisms by which stones develop in the kidney are poorly understood. Renal tubular fluid is normally supersaturated with calcium and oxalate ions which can nucleate to form crystals of calcium oxalate monohydrate (COM). However, this fact alone does not explain how these crystals are retained in the nephrons of the kidney and produce stones. Moreover, some doubt that crystal formation, per se, results in stones, in part because calculations based on the rate of crystal growth and flow of tubular fluid suggest that a nascent crystal could not become large enough to occlude a tubule lumen during the time required for transit through the nephron. To resolve this problem and explain how stones form, there is speculation that either several small crystals aggregate to form a mass large enough to block a tubule, or small crystals bind to the tubular epithelial cell surface where they accumulate. Otherwise crystals would leave the nephron suspended in the flowing tubular fluid, and kidney stones would not develop from crystals.

Urinary COM crystals are implicated in kidney stone disease, and several different lines of investigation emphasize the importance of crystal-cell interactions in the pathogenesis of nephrolithiasis. Associations between crystals in tubular fluid and renal epithelial cells appear to take place in vivo. Papillary casts are often found in kidney stones, and Randallis plaques are known to form in the renal papillae during crystalluria. Recent investigations show that COM crystals, the most abundant constituent of kidney stones, can rapidly adhere to the surface of kidney tubular cells, undergo internalization, and stimulate gene expression, cytoskeletal reorganization and mitogenesis.

Information on the responses of kidney tubular epithelial cells to COM crystals was provided by observation of humans with hyperoxaluria. Hyperoxaluria can be classified as either primary or secondary and is often associated with interstitial fibrosis and renal failure. Primary hyperoxaluria is a genetically distinct inborn error of oxalate metabolism, whereas secondary hyperoxaluria occurs in several gastrointestinal malabsorptive states, during pyridoxine deficiency, and following ethylene glycol ingestion and methoxyflurane anesthesia. Intracellular calcium oxalate crystals and proliferating tubular cells were noted in human tissue biopsied from a normal kidney 16 days after it was transplanted into a patient with primary hyperoxaluria, and engulfment of calcium oxalate crystals and tubular cell proliferation were also reported in a patient with hyperoxaluria and acute renal failure associated with Crohn's disease. Crystals were observed within tubular epithelial cells and were associated with proliferation and the formation of multinucleated giant cells. Adhesion of crystals to the apical surface of tubular cells was noted by scanning electron microscopy performed on renal tissue from a patient with hyperoxaluria. The importance of the plasma membrane in crystal-cell interactions was also suggested by the observation that membrane fragments of renal epithelial cells promote crystallization from supersaturated calcium oxalate solutions.

Calcium oxalate crystals, when deposited in the interstitium, can cause marked inflammation and fibrosis of the renal parenchyma. An autopsy study of persons with normal kidney function, acute renal failure or chronic renal failure revealed that the incidence and severity of tubular and interstitial calcium oxalate deposition was a function of the duration of renal failure which in turn is correlated with an elevated plasma oxalate concentration. Therefore calcium oxalate deposits in the kidney are associated with both interstitial fibrosis and loss of renal function. Crystal endocytosis might occur to a lesser extent in the kidney of normal individuals than in those who form stones.

In an animal model, severe hyperoxaluria induced in rats by an intraperitoneal injection of sodium oxalate immediately produces intraluminal calcium oxalate crystals which attach to the apical membrane of renal tubular epithelial cells and subsequently appear as deposits in the interstitium of the kidney. One possible scenario based on current experimental evidence is that during periods of hyperoxaluria COM crystals can nucleate and grow within tubules, bind to tubular cells, undergo endocytosis, and initiate release of factors from tubular cells that could stimulate fibroblast proliferation by a paracrine pathway and ECM accumulation via the plasmin system. The end result of this pathway is interstitial fibrosis and progressive kidney failure.

The in vitro interaction between kidney cells and crystals was elucidated by utilizing a model system of high-density, quiescent cultures of nontransformed monkey renal epithelial cells (BSC-1 line) to simulate the tubular epithelium. These cultures are prepared by allowing cells to completely cover the surface of a culture dish and then reducing their growth to a minimal level by lowering the concentration of serum to 0.01% in the medium. Exogenous COM crystals irreversibly bound to the cells in culture within as little as 15 seconds, were subsequently endocytosed, and often stimulated proliferation. BSC-1 cells appear to survive and divide in culture despite the presence of internalized COM crystals, providing evidence that the crystals are not toxic for these renal cells. COM crystals are more avidly internalized by BSC-1 cells than two other calcium-containing crystals, hydroxyapatite (HA) or brushite (BR). Given the different molecular structures of crystalline surfaces, it is possible that the affinity of COM crystals for the cell surface is greater than it is for HA or BR crystals. In fact, COM crystals are mitogenic for cultured renal epithelial cells of the BSC-1 and MDCK lines, a unique property not shared by another calcium-containing crystal (brushite) or by latex beads. The uptake of COM crystals by BSC-1 cells is a regulated event which can be modified by diverse signals. The mitogens epidermal growth factor (EGF), adenosine diphosphate (ADP) and calf serum each increase COM crystal endocytosis, whereas urinary Tamm-Horsfall glycoprotein (THP), heparin, transforming growth factor TGF-β2, and the tetrapeptide arginine-glycine-aspartate-serine (SEQ ID NO:1) (RGDS) inhibit it. Thus renal epithelial cells respond in a specific pattern to a crystal commonly found in urine, and these responses can be modified by extracellular signals. The appearance of crystals in vivo is similar to those of BSC-1 cells in culture, a nontransformed renal epithelial cell line derived from the African green monkey, suggesting that BSC-1 cells in vitro are a model for renal tubular cell interactions with COM crystals in vivo.

When used as an in vitro system to study the renal cell-crystal interaction, COM crystals were observed to adhere to BSC-1 cells after as little as 15 seconds, far less than the estimated 3–5 minutes required for filtrate to traverse the length of the nephron. Crystals might have prolonged contact with the kidney tubular lining cells in vivo if fluid travels within the tubule in a laminar fashion, as has been proposed, and the flow rate adjacent to the epithelial cell surface approaches zero.

When the most common type of crystal in kidney stones, COM, was added to cultures of monkey kidney epithelial cells (BSC-1 line) 19% of the cells internalized a crystal after 30 minutes.

Endocytosis of COM crystals by cultured renal epithelial cells is regulated by diverse molecules, suggesting that in vivo along the nephron, the outcome of crystal-cell interactions could be determined by the balance between positive EGF, ADP and negative factors (fibronectin, TGF-β2) such as those discussed herein. Endocytosis may be mediated in part by a specific cell surface receptor.

Nontransformed monkey renal epithelial cells (BSC-1 line) do not perceive crystals as inert, but respond by displaying a program of specific events including binding of the crystal to the cell surface, crystal endocytosis, protooncogene expression, reorganization of actin filaments and cytokeratine-containing intermediate filaments, DNA synthesis, and, in some instances, cell multiplication. The response of renal epithelial cells to COM crystals is characterized by increased expression of specific genes which encode transcriptional activators (c-myc, EGR-1, Nur-77, and c-jun), a regulator of the extracellular matrix (ECM) composition (PAI-1), and growth factors (platelet-derived growth factor [PDGF]-A chain and connective tissue growth factor [CTGF]). The protein products of these genes (PAI-1, PDGF-A chain, CTGF) could contribute to interstitial fibrosis observed in kidneys of patients with primary or secondary hyperoxaluria.

The presence of cell-surface binding sites for COM crystals was suggested by investigations utilizing primary cultures of rat medullary cells. Binding was a saturable process that was partially antagonized by HA crystals. Further study revealed that cells which avidly bound crystals expressed basolateral surface antigens on their apical surfaces. Additional support for specific plasma membrane crystal-binding sites was obtained by treating cells with EGTA which exposed basolateral epitopes and permitted increased COM crystal binding. These experiments, and the observation that COM crystals bind to injured regions of rat bladder epithelium suggest that crystal-binding sites may be minimally exposed under physiological circumstances, but are unmasked when cells are injured, or possibly during regeneration after injury. Specific soluble factors may also modify crystal-cell interactions. In a study of crystal-induced lysis of red blood cells, known inhibitors of crystal growth such as citrate and pyrophosphate were shown to decrease attachment of COM, HA, and monosodium urate crystals to the plasma membrane. The response of a renal epithelial cell to a urinary crystal may not be determined solely by the interaction at the plasma membrane, but may be modulated by biological signals.

The interaction of COM crystals with kidney cells in culture can result in specific responses such as binding to the apical cell surface, internalization, and in some cells initiation of proliferation. Each of these three responses appears to be under the control of a different set of extracellular factors. Crystal binding to the apical plasma membrane can be blocked by diverse anions found in urine such as the glycoproteins nephrocalcin and uropontin, specific glycosaminoglycans, and citrate. After crystals adhere they can be internalized by the cells, a process which can be stimulated (by e.g., EGF, ADP, calf serum)., or inhibited (by e.g., THP, heparin, TGF-β2, RGDS). The capacity of THP, fibronectin or heparin to inhibit endocytosis was mediated by an interaction of these molecules with cells, not by coating the crystals. Thus renal epithelial cell endocytosis of COM crystals is regulated by diverse molecules including THP, the most common protein found in human urine. Uptake of COM crystals is associated with an increased probability of cell division, and the internalized crystals can apparently be distributed to daughter cells at mitosis. In addition, the crystals can persist for at least two weeks within the cells suggesting that they are not perceived as toxic. The cell-crystal interaction can stimulate expression of specific genes whose products may contribute to some of these processes, such as cell growth and accumulation of ECM constituents.

Specific responses to crystals also occur in nonrenal cells. Basic calcium phosphate crystals induce c-fos and c-myc protooncogene expression and initiate mitogenesis in Balb/3T3 fibroblasts. A role for cytokines in cell-crystal interactions has also been reported. Monosodium urate, calcium pyrophosphate dihydrate, and hydroxyapatite crystals each stimulated interleukin (IL)-6 production by synoviocytes and monocytes grown in culture, and monosodium urate crystals trigger release of IL-8 from cultured monocytes.

The plasminogen-activating system plays a key role in regulating the extracellular matrix (ECM) composition. Because progressive accumulation of extracellular proteins is a central feature of interstitial fibrosis, genes which regulate the components of the plasminogen-activating system were studied in renal epithelial cells of the BSC-1 line exposed to COM crystals. Plasmin is an extracellular broad-spectrum protease that is activated when its precursor, plasminogen, is cleaved. Plasminogen is the target of two other highly specific proteases, urokinase-type plasminogen activator (u-PA) and tissue-type plasminogen activator (t-PA). u-PA is primarily responsible for plasmin generation in processes involving degradation of ECM and basement membranes. Fast-acting plasminogen activator inhibitor (PAI-1) regulates plasmin activity by blocking the action of UPA which decreases formation of plasmin. Reduced plasmin production could thereby permit accumulation of ECM proteins. When Northern analysis was used to study gene expression, PAI-1 was induced and u-PA was unchanged in renal cells exposed to COM crystals. Increased expression of PAI-1 without a change in u-PA could result in decreased plasmin production and enhanced accumulation of ECM proteins so that eventual fibrosis is the predicted result. Augmented expression of the gene encoding PDGF-A chain was also detected. Increased availability of PDGF in the extracellular space would favor fibrosis. CTGF is a peptide originally identified as a secreted product of human vascular endothelial cells that has properties similar to PDGF; it is mitogenic and chemotactic for connective tissue cells such as fibroblasts and smooth muscle cells. Induction of the transcript for CTGF at one hour after exposure to crystals and its persistent expression for the next twenty three hours suggests that secreted CTGF protein could stimulate fibroblast proliferation in a paracrine manner, as does PDGF. Of 15 genes studied which regulate ECM composition, only three (PAI-1, PDGF-A chain, CTGF) exhibited increased expression after exposure of the cells to COM crystal. These results suggest that stimulated gene expression in this setting is highly targeted within the genome.

Early structural and functional changes at the kidney epithelial cell surface were identified during an interaction between a COM crystal and cultured BSC-1 cells. [14C] COM crystals bind to the cell surfaces within seconds. Scanning electron microscopy (SEM) was used to examine the structural correlates of COM crystal binding to the apical membrane of BSC-1 cells. Under low power, the outline of individual cells, nuclei and surface microvilli were seen, as well as small adherent crystal aggregates. Higher magnification revealed contact between microvilli and the crystal surface. At the base of the same microvillus small cellular- .extensions could be seen over the surface of the crystal. In other instances extended microvilli covered a substantial portion of the crystal. These microvillar processes appeared to subsequently coalesce and completely cover the crystal. At later times apparent crystal aggregates were observed immediately beneath the plasma membrane. Microvilli on the surface of macrophages appear to contribute to phagocytosis in a similar manner.

Transmission electron microscopy (TEM) was used to visualize intracellular changes as COM crystals were engulfed. Crystals adherent to microvilli were noted. Microvillar processes appeared to extend sequentially to occupy a sizable portion of the crystal surface. Inside cells crystals appeared within membrane-lined vacuoles. Lysosomes were located in the vicinity of intracellular crystals at 3 hours and after 12 hours small crystals were seen within the organelle.

Cytoskeletal responses to crystal uptake were sought by immunofluorescence microscopy which revealed concentration of F-actin at sites of crystal contact as well as a generalized reorganization of the intermediate filament network containing cytokeratin 8.

COM crystals are mitogenic for BSC-1 cells. The fate of crystals in cells going through mitosis was elucidated as follows: Subconfluent cultures of BSC-1 cells were prepared and crystals (50 μg/ml) were added on day zero. On day 1 the medium was changed to remove any nonadherent crystals. The number of cells in the culture containing one or more crystals increased between 1 and 7 days (P<0.001), although no additional crystals were added after day 0, demonstrating that internalized crystals were passed on to daughter cells during division. Furthermore, the presence of intracellular crystals did not adversely affect cell growth.

Four signals were identified which alter cellular function, are mitogenic for BSC-1 cells and stimulate endocytosis of COM crystals, although the pathways by which they do so likely differ. The concentrations of EGF and ADP that enhance endocytosis are much below those that initiate DNA synthesis. Two of the regulatory signals identified modify cell structure. Exposure of BSC-1 cells to ADP for 2 minutes induces marked changes in cell shape and reorganization of the intermediate filaments containing cytokeratin 8. A low-potassium (K) environment initiates functional changes in the plasma membrane within seconds, and an increased number of surface microvilli within 3 minutes. Thus when cells are exposed to ADP or low-K medium the cytoskeleton appears to play a role in generating the observed structural changes, and might also mediate crystal uptake.

Factors that regulate endocytosis of COM crystals by kidney epithelial cells are important to identify because increased understanding of mechanisms which mediate formation of a renal calculus can lead to diagnostic assays and treatment for this disease, for example, by use of crystal adhesion inhibitors.

Preventing crystal adhesion to the cell surface is a means to block the cascade of events that results in crystal retention and nephrolithiasis. As illustrated in FIG. 5, by scanning (SEM) and transmission electron microscopy (TEM), COM crystals are seen to first make contact with microvilli on the apical surface of BSC-1 cells. Subsequently, crystals are visualized within membrane lined vesicles, which in some instances fuse with lysosomes. These observations suggest an affinity between the crystals and the kidney cell surface that provokes a cellular response. (Lieske et al., 1994).

SUMMARY OF THE INVENTION

A composition which disrupts the cascade of events that results in crystal retention and nephrolithiasis is the crystal adhesion inhibitor (CAI) of the present invention, a composition which is a sialic acid-containing anionic glycoprotein having an estimated molecular weight of 39,000 daltons based on SDS polyacrylamide gel electrophoresis. The sialic acid residues are important in maintaining a negative charge, because the amino acid composition of the inhibitor predicts a net near-neutral charge.

Renal epithelial cells constitutively produce the factor (CAI) that prevents adhesion of COM crystals to their apical surface. Sequence information for 124 amino acids of the $NH_2$-terminus and 6 internal fragments of this novel core protein has been obtained, and used to prepare 2 monospecific antibodies against 2 different synthetic peptides.

The inhibitor is purified by a novel crystal-affinity method wherein the anionic, hydrophobic material adheres to the crystals from which it is later removed by, e.g., EDTA. This is followed by purification using SDS-PAGE and electroblotting or electroelution of the gel or reversed-phase HPLC. The purified CAI is an anionic glycoprotein. The presence of carbohydrate is manifested by a loss of inhibitory activity following exposure of CAI to neuraminidase, indicated the critical functional importance of its anionic sialic acid residues. Its carbohydrate character is confirmed by the detection of uronic acid using the carbazole reaction, and a positive test using a DIG glycan kit. Its protein character is established by amino acid compositional analysis and amino acid sequence information, and is supported by positive reactions in the presence of ninhydrin or bicinchoninic acid (BCA). Its activity is resistant to pH 2, freezing and thawing. The near neutral net charge of the CAI protein distinguishes it from known strongly anionic proteins that block adhesion of COM crystals to the surface of renal epithelial cells.

Availability of the CAI permits comparative screening for other candidate inhibitors of crystal adhesion. Generally, those at least as active in preventing crystal adhesion to cells, are selected for further processing. The tissue culture system of the present invention is contacted with a candidate agent, and the degree of inhibition of crystal adhesion to cells in a control culture are each compared to a culture treated with CAI as a standard.

Assays based on crystal adhesion are useful for identifying patients at high risk for kidney stone disease and for screening for drugs which prevent crystal adhesion. Polyclonal antibodies developed against the CAI by standard methods are used to quantitate the amount of CAI in a sample of urine from an individual with untreated or treated nephrolithiasis, or who is suspected of having this condition.

For characterization of the CAI, a monospecific polyclonal antiserum is preferable to monoclonal antibodies because the latter each complex with single antigenic determinants, whereas a polyclonal antiserum likely recognizes multiple sites on the target molecule. Because CAI is a glycoprotein and neuraminidase treatment inhibits its function, it is likely that sialic acid residues are present at its "active site(s)", the sites by which the CAI binds to crystal surfaces or cell surfaces to block crystal adhesion. Thus a polyclonal antiserum which contains IgG molecules that recognize antigenic determinants composed of carbohydrate, protein, or both is a particularly useful reagent. Whereas a monoclonal antibody might recognize antigenic sites on the CAI molecule which are not important for its biologic function, a polyclonal antibody is more likely to block activity when it is recognized and binds to CAI. Monospecific antibodies have been prepared to two synthetic peptides having sequences identified in CAI. Monoclonal antibodies can also be prepared to functionally active fragments of the CAI used as immunogens employing techniques well-known to the art.

To determine the minimum amount of the molecule necessary to elicit biological activity, that is, the minimum peptide that includes the "active site or sites," CAI that has been isolated and purified as described herein is subjected to enzymatic cleavage which produces fragments. The fragments are then tested for biological activity according to the methods described herein. It is likely that the active site or sites will include sialic acid residues. The relative efficiency of the active-site containing fragments is also of interest because even though biologically active, some fragments are likely to be more active than others, e.g. a heparin molecule of 5,000 daltons molecular weight is not as efficient as a heparin molecule of 18,000 daltons molecular weight. Inhibitors are designed to complex with the active site(s) as determined by the methods discussed above.

Susceptibility to stone formation varies among individuals. This variation is likely due to inherent variations among individuals in the ability to produce inhibitor, which is measurable and provides a means for classifying persons according to risk of developing stones. If an immunological assay detects no CAI or an amount of CAI less than the value in nonaffected control individuals, the patient is considered to be at increased risk of kidney stone formation. This assay is also useful for monitoring the success of therapeutic regimens designed to treat or prevent the appearance of new stones which may be directly correlated to the urinary concentration of CAI in specific individuals. The amount of CAI detected by the immunological assay and its functional capacity to inhibit adhesion of COM crystals to kidney epithelial cells in culture is used to classify patients with nephrolithiasis. A tissue culture system containing kidney epithelial cells is used to quantitate the function of the CAI or its equivalent.

Novel molecular tools are now available to seek the cDNA sequence of CAI. Amino acid sequence information now available (124 residues) permits studies using a polymerase chain reaction (PCR) strategy, whereas the two monospecific antisera are useful in an immunoscreening approach to obtain a cDNA sequence.

After the DNA sequence of the gene encoding CAI is obtained, further study of the protein and the factors that regulate its production will improve understanding of kidney stone formation. In certain individuals, defective production of CAI likely predisposes to kidney stone formation. In CAI-deficient patients, adhesion of crystals to tubular cells is expected to occur more readily, and once retained in the nephron, such crystals likely grow into kidney stones. Therefore, study of CAI could yield important new insights into the pathogenesis of kidney stone formation, and lead to development of a novel form of therapy by using knowledge about CAI structure and function.

To summarize uses of CAI:

1. Urine from a patient is tested to detect defective CAI or other anti-adhesion factors in urine by using the crystal adhesion assay described herein.
2. Diverse chemical and pharmaceutical agents are selected because they exhibit characteristics similar to CAI, and are tested for their ability to prevent crystal adhesion to cells as compared to CAI.
3. The structure of CAI provides a basis for the rational design of effective drugs, for example, an active domain of the CAI molecule that is smaller than the native molecule in size may be used to prevent crystal adhesion.
4. CAI is used as a drug to prevent stones: delivery is via liposome, intravenous or subcutaneous injection, or intranasal systems. Chemical modification of CAI may permit its use by an oral route.
5. Monospecific antibodies to purified CAI or peptide fragments of CAI are provided for detection and quantitative assays of CAI.
6. Hybridization of CAI cDNA with samples of DNA from individuals is used to screen for defective CAI carriers who are candidates for stone disease. Sloughed renal tubular cells isolated from urine or white blood cells from peripheral blood are suitable samples for this hybridization test.
7. If a crystal-binding receptor is identified on a cell surface, sloughed renal tubular cells could be screened for an abnormal quantity/quality of the receptor.

BRIEF DESCRIPTION OF THE DRAWINGS

FIG. 6 lists the amino acid sequences of CAI fragments, the amino terminus and 6 interval fragments.

FIG. 7 shows homology of the amino-terminal fragment of CAI to 2 other proteins found in GenBank.

DESCRIPTION OF THE PREFERRED EMBODIMENT

Figure 1:
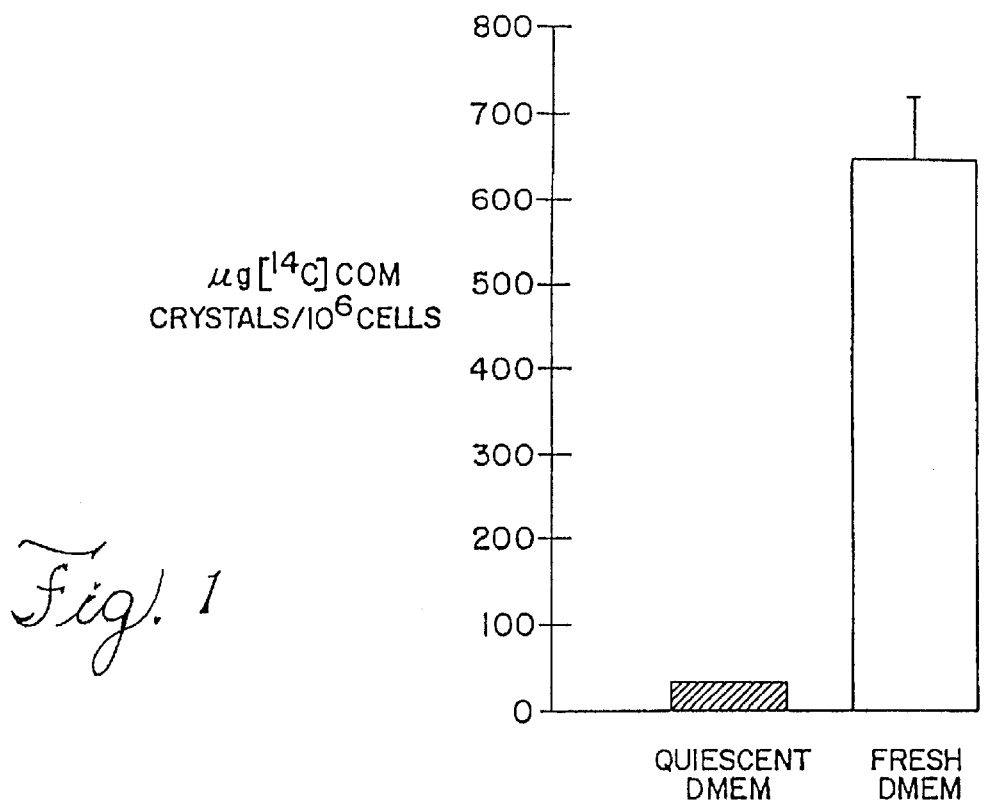
FIG. 1 illustrates inhibition of COM crystal adhesion by medium conditioned by BSC-1 cells.

Kidney epithelial cells release a factor that blocks adhesion of COM crystals to their apical surface. This molecule has been named Crystal Adhesion Inhibitor, or CAI. Kidney epithelial cells in culture constitutively produce CAI suggesting that cells lining the nephron may do likewise in the intact human kidney. Molecular characterization suggests that CAI is a strongly anionic glycoprotein with an apparent $M_r$ of 39,000 Da. Microsequencing of the amino terminus and 6 fragments has identified a total of 124 amino acids and reveals that CAI is novel. The amino acid sequence information has been utilized to prepare two synthetic peptides. Rabbit monospecific antisera raised against these peptides recognize CAI on Western blots of partially-purified conditioned medium and a protein of the same size in a total cell lysate.

A fresh insight into the pathogenesis of nephrolithiasis is the foundation of the present invention, that is, that CAI secreted by cells along the nephron protects the cells from interacting with COM crystals that nucleate in the tubular fluid of virtually all individuals. Thus, the CAI prevents nascent crystals from binding to tubular cells and thereby blocks the cascade of events that results in crystal retention and formation of kidney stones. The crystals routinely formed then pass harmlessly out of the nephron.

Monospecific antibodies to CAI or CAI peptide fragments are used to measure the amount of CAI in urine and/or blood of patients with stone disease. The urinary excretion and/or serum concentration of CAI is lower in certain patients with stone disease compared to non-stone-formers. A threshold is determined for the quantity of CAI in various groups such as stone-formers and nonstone-formers. The threshold is then applied to diagnostic assays to determine an "at risk" ratio. This diagnostic strategy identifies stone-formers with insufficient or possibly dysfunctional CAI and classifies them by quantitative and functional assessment of endogenous inhibitor. Classification of a patient's disease according to these criteria is predictive of the appropriate treatment regimen. The structure and function of CAI provides a model for the design of more effective therapeutic agents. The tissue culture system described herein permits rapid screening of potential (candidate) agents for preventing stone disease. An agent's capacity to inhibit adhesion of radioactive COM crystals to renal epithelial cells is measured and compared to purified CAI. Agents that are at least as effective inhibitors as CAI are rapidly tested in animal models of nephrolithiasis and subsequently in patients with this condition.

The acute hyperoxaluria model induced in the rat can be used to study the capacity of CAI to prevent adhesion of COM crystals to the surface of tubular cells. Male Sprague-Dawley rats are given a single intraperitoneal injection of sodium oxalate to induce the formation of calcium oxalate crystals. At specified times thereafter the kidneys are fixed and examined for retention of crystals within the nephron by light microscopy, and by scanning and transmission electron microscopy (Khan and Hackett, 1991).

Due to its ability to block crystal adhesion to renal epithelial cells, purified CAI is available for use as a drug to prevent kidney stone formation. To exert an effect, CAI must be delivered to the nephron lumen. For example, CAI present in peripheral blood and filtered by the glomerulus, would appear in the tubular fluid and exert an anti-adhesion effect. Methods known to those of skill in the art to systemically administer a protein of this size include a liposome delivery system, intravenous or subcutaneous injection, and intranasal application. cDNA for CAI may be introduced into a viral vector which is administered to individuals with defective CAI as a form of gene therapy to allow the patient's own renal tubular cells to produce biologically active inhibitor.

Crystal Adhesion Inhibitor

Surprisingly, adhesion of [14C]COM crystals to confluent cultures of BSC-1 cells bathed in fresh medium or phosphate-buffered saline (PBS) was about 15-fold greater than in cultures exposed to conditioned medium. The conclusion from this observation was that the conditioned medium contained abundant crystal adhesion inhibitory activity released by the cells. Crystal adhesion inhibitory activity was then sought in medium conditioned by high-density cultures after the 3 days required for growth quiescence to occur in these cultures. Results shown in FIG. 1 were obtained after high-density, quiescent cultures were prepared and the medium was aspirated and replaced with either fresh medium (open bar) or medium from other quiescent cultures (black bar). [$^{14}$C]COM crystals (200 μg/ml) were added and two minutes later the monolayer was washed 3 times with PBS, then scraped directly into a scintillation vial and radioactivity was measured.

Crystal binding was markedly reduced when quiescent medium rather than fresh medium was present. Each value is the mean±SE for three cultures.

Figure 2:
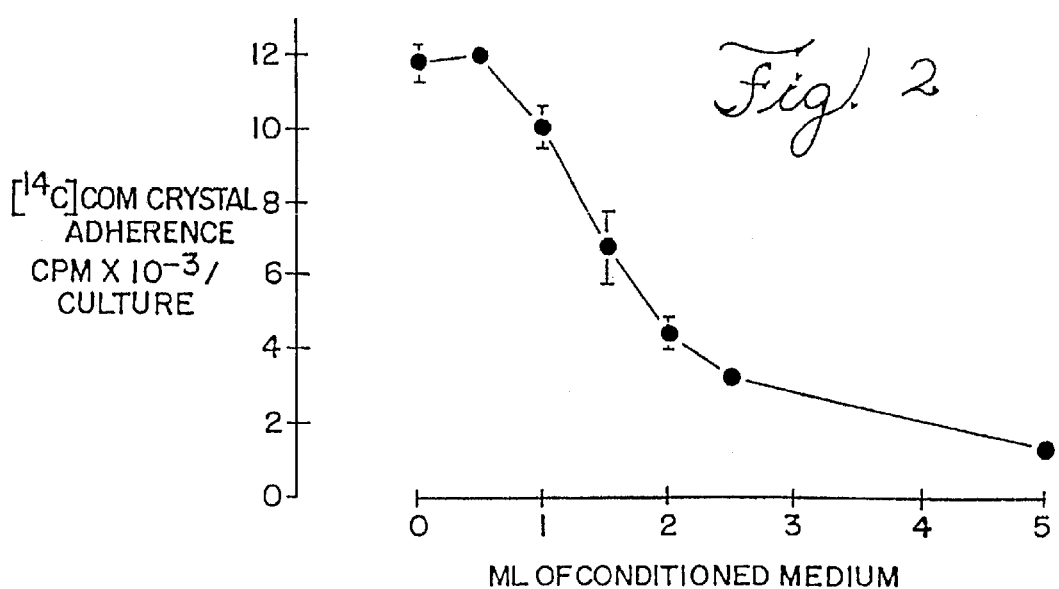
FIG. 2 illustrates inhibition of COM crystal adhesion by incremental addition of medium conditioned by BSC-1 cells.

FIG. 2 quantifies the amount of crystal adhesion inhibiting activity released by kidney epithelial cells. High-density, quiescent cultures were prepared and the medium aspirated and replaced with PBS to which a specified quantity of conditioned medium was added (0 to 5 ml). [$^{14}$C]COM crystals were added (200 μg/ml) and 2 minutes later the buffer was removed, the cell layer was rinsed three times, and cell associated radioactivity was measured. COM crystal binding was progressively diminished by addition of increasing amounts of conditioned medium, with near maximal inhibition occurring with addition of more than 2.5 ml. Each point is the mean+SEM for six cultures.

1. Isolation and Purification of an Inhibitor

A novel purification protocol was developed to isolate crystal adhesion inhibitory activity secreted by the kidney cells. The method uses the crystals as an affinity purification reagent. Activity bound to the crystals is released by dissolving the crystals with EDTA. Reversed-phase HPLC or SDS-PAGE have each confirmed the presence of a single molecular species that is an anionic, sialic acid-containing glycoprotein having an $M_r$ of 39,000 daltons. The purified material exhibits crystal adhesion inhibitory activity, and is called the Crystal Adhesion Inhibitor (CAI).

Initially, to isolate the crystal adhesion inhibitor (CAI), medium from 3-day quiescent cultures of BSC-1 cells containing 0.01% calf serum was collected and then passed through a 0.22-μm filter to remove any cells or debris. The conditioned medium which contains CAI complexed with COM crystals, was then subjected to ultracentrifugation through a YM 30 membrane (Amicon) to eliminate molecules with an apparent $M_r$ of <30,000. The retained material was loaded onto a DEAE sepharose anion exchange column (Pharmacia) that was eluted with 0.4 M NaCl. Na EDTA (Sigma) was then added to the eluate to achieve a final concentration of 50 mM to cause disassociation of CAI from the crystals. Two days later the eluate was applied to a Biogel A 0.5M column (100–200 mesh, 1.5×90 cm) equilibrated with 10 mM Tris, 40 mM choline chloride at pH 7.4. The column is eluted at 4° C. with the same buffer at a flow rate of 15 ml/hr and 3 ml fractions were collected.

The fractions were assayed for crystal adhesion inhibitory activity using the crystal adhesion assay for candidate inhibitors described herein. COM crystals (100 mg) were equilibrated with a supersaturated calcium oxalate solution in water. Fractions to be tested for activity were added to the calcium oxalate solution containing crystals and incubated overnight in 2 ml tubes subjected to end-over-end rotation. The next day crystals were washed in succession with supersaturated calcium oxalate solution (2 ml) containing no NaCl, 1 M Na Cl, and then 4 M NaCl (twice) each for one hour. Washed crystals were then incubated with 10 mM Tris, 40 mM choline chloride (pH 8) containing 50 mM EDTA, and this solution was replaced daily and accumulated until the crystals were dissolved. After dissolution of the crystals, pooled material was placed in Spectra/por dialysis tubing (12–14,000 M, cutoff and dialyzed at 4° C. against 10 mM sodium phosphate buffer. The dialyzed material was volume-reduced with a Centricon 10 concentrator (Amicon) and assayed for activity as described herein.

Another protocol to isolate CAI by COM crystal affinity is that pooled fractions containing crystal-aggregating activity eluted from a Biogel sizing column were combined, concentrated and rinsed using a Centricon-30 microconcentrator, and incubated with COM crystals overnight. The next day crystals were washed in succession with a supersaturated calcium oxalate solution containing no NaCl, 1 M NaCl, and finally 4 M NaCl (twice). Then crystals were dissolved with 250 mM Na EDTA to release crystal-adherent molecules. The crystal-bound material was dialyzed against 10 mM sodium phosphate buffer to remove EDTA. Material eluted from the crystals inhibited adhesion of COM crystals to BSC-1 cells, whereas material produced by dissolution of control crystals (not coated with CAI) did not exhibit crystal adhesion inhibitory-activity. CAI isolated by dissolution of COM crystals produced a single sharp band with an apparent $M_r$ of 39,000 when resolved by SDS-PAGE (20% polyacrylamide) under reducing conditions.

2. Characteristics of CAI

Characteristics of the crystal adhesion-inhibitory activity in conditioned medium indicated that CAI is resistant to freezing, heating to 56° C. for 30 minutes, or boiling for 10 minutes. Treatment with either trypsin (100 µg/ml, 37° C., pH 7.4, 4 hours), proteinase K (100 µg/ml, 55° C., pH 7.4, 3 hours) or dithiothreitol (65 mM, 22° C., 1 hour) does not abolish activity (these tests are described in Walsh-Reitz et al., 1986). Additional information obtained by amino acid compositional and sequence analysis presented herein indicates that purified CAI is indeed a protein. Interestingly, its crystal adhesion inhibitory activity continues to be expressed in peptide fragments or structurally altered forms of the molecule generated by exposure to trypsin or proteinase K. The lack of effect of dithiothreitol suggests that intact intra- or intermolecular disulfide bonds are not required for CAI activity. Treatment with heparinase 1 (5 U/ml, 37° C., pH 7.4, 4 hours), Heparinase III (0.5 U/ml, 43° C., pH 7.4, 4 hours) (Linker and Hovingh, 1972) or chondroitinase ABC (0.5 U/ml, 37° C., pH 7.4, 4 hours) (Yamamata et al., 1968) each failed to abolish activity, as did treatment with DNAse (10 ng/ml, 23° C., pH 7.4, 1 hour) or nitrous acid (0.25 M, 23° C., pH 7.4, 2 hours) (Carey and Evans, 1989). These observations suggest that neither intact heparan sulfate, chondroitin sulfate or DNA is required for crystal adhesion inhibitory activity. Loss of activity after treatment with neuraminidase (1 U/ml, pH 5.5, 37° C., 1 hour) (Vorbadt, 1989) or sodium hydroxide (0.2 M at 23° C., 18 hours), a positive carbazole reaction (Bitter and Muir, 1962) and a DIG glycan detection kit used as directed by the manufacturer (Boerhinger Mannheim) each suggested that the factor contains carbohydrate. Thus, CAI activity is associated with the presence of carbohydrate, and sialic acid residues are required for its function.

Crystal adhesion inhibitory activity is detectable in the conditioned medium of BSC-1 cells one day after incubation in quiescent medium (0.01% calf serum), and progressively more activity is present on days 2 and 3, with a maximum at 3 days. Following concentration using the YM 30 membrane (Amicon), the retained CAI activity (>30,000<100,000 daltons) tested positive for the presence of carbohydrate using the DIG Glycan kit (Boerhinger Mannheim). When this isolate was subsequently eluted from the DEAE Sepharose anion-exchange column, CAI activity gave a positive carbazole reaction suggesting the presence of uronic acid/carbohydrate moieties. The quantity of CAI tested, which was biologically active, gave a carbazole reaction equivalent to that of 10 µg of heparin. CAI was then eluted from the Biogel A 0.5M column and displayed an apparent molecular weight of between 60,000–100,000 daltons, with a peak of activity at an apparent M, of 80,000 daltons. However, when the DEAE eluate was incubated with EDTA for 2 days, CAI eluted from the Biogel column in a sharp peak with an apparent $M_r$ of 15,000 daltons suggesting that EDTA treatment disaggregated complexes of biologically active CAI molecules and thereby reduced the apparent size of CAI eluted from the column.

Biologically active crystal adhesion inhibitor (CAI) purified from the conditioned medium of BSC-1 cells was subjected to reversed-phase high pressure liquid chromatography (RP HPLC) on a C4 column (Vydac) which yielded a single, sharp peak when eluted with an acetonitrile gradient (1 to 80%) in trifluoroacetic acid (0.1%). The material in this peak was dried and then hydrolyzed with 6 N HCl for 24 hours at 120° C. in vacuo. The hydrolysate was then subjected to amino acid compositional analysis. The starting material in one experiment was estimated at $42 \times 10^{12}$ moles (1.63 µg) of a protein having a molecular size of 39,000 daltons based on its migration velocity during SDS-polyacrylamide gel electrophoresis. Amino acid composition expressed as mole % is shown in FIG. 6. The primary structure of the protein may be defined by sequential degradation of its $NH_2$ terminus using the Edman reagent, phenyl isothiocyanate (PITC), followed by automated gas phase microsequencing.

Two additional independent isolates of CAI yielded similar results.

TABLE 1

Amino Acid Composition of Crystal Adhesion Inhibitor, Nephrocalcin, and Uropontin.

| Apparent $M_r$ | CAI 39,000 | Nephrocalcin 14,000 | Uropontin 50–72,000 |
|---|---|---|---|
| Amino Acid | | | |
| Aspartic Acid/asparagine | 6.4[1] | 20.1 | 20.7 |
| Threonine | 4.1 | 6.3 | 6.6 |
| Serine | 10.4 | 9.1 | 16.2 |
| Glutamic acid/glutamine | 13.2 | 13.2 | 14.0 |
| Proline | trace | 5.8 | 5.5 |
| Glycine | 18.4 | 7.2 | 6.9 |
| Alanine | 7.3 | 3.7 | 5.2 |
| Valine | 3.9 | 7.2 | 4.6 |
| Cysteine | trace | 2.2 | 0 |
| Methionine | trace | 2.3 | .7 |
| Isoleucine | 4.6 | 1.8 | 1.5 |
| Leucine | 8.6 | 5.6 | 4.7 |
| Tyrosine | 2.2 | 1.7 | 2.6 |
| Phenylalanine | 3.6 | 2.4 | 1.6 |

TABLE 1-continued

Amino Acid Composition of Crystal Adhesion Inhibitor, Nephrocalcin, and Uropontin.

| Apparent $M_r$ | CAI 39,000 | Nephrocalcin 14,000 | Uropontin 50–72,000 |
|---|---|---|---|
| Lysine | 7.0 | 4.1 | 3.9 |
| Histidine | 3.9 | 3.0 | 3.6 |
| Arginine | 6.6 | 3.3 | 1.7 |
| Tryptophan | not done | 1.0 | not done |
| Total | 100.2 | 100.4 | 100.0 |
| Total net negative charge[2] | −2.1 | −22.9 | −25.5 |

[1]Values are mole %.
[2]Total net charge on the protein core of each molecule was calculated by assuming that all aspartic acid plus asparagine and glutamic acid plus glutamine residues are anions, and that all histidine, lysine and arginine residues are cations.

Abbreviations:
A: Ala, Alanine.
C: Cys, Cysteine.
D: Asp, Aspartic acid.
E: Glu, Glutamic acid.
F: Phe, Phenylalanine.
G: Gly, Glycine.
H: His, Histidine.
I: Ile, Isoleucine.
K: Lys, Lysine.
L: Leu, Leucine.
M: Met, Methionine.
N: Asn, Asparagine.
P: Pro, Proline.
Q: Gln, Glutamine.
R: Arg, Arginine.
S: Ser, Serine
T: Thr, Threonine.
V: Val, Valine.
W: Trp, Tryptophan.
Y: Tyr, Tyrosine.
X: no definite assignment; possibly a glycosylated amino acid.
( ): uncertainty about assignment of amino acid at this position

3. Amino Acid Sequencing

Since amino acid compositional analysis suggested that CAI differed from two known urinary proteins (Table 1) additional electroblots of CAI were prepared for amino acid microsequencing by Edman degradation to better determine if it was novel. Results of microsequencing of the amino terminus of CAI, performed at the University of Chicago Amino Acid and Protein Core Lab, are shown in FIG. 6. To allow more complete characterization of CAI, and confirm that it was novel, additional electroblots of CAI were prepared to perform proteolytic cleavage and microsequencing of the resulting fragments. Lys-C protease cleavage of electroblotted CAI (Fernandez et al. 1994) was performed at the Rockefeller University Protein Sequencing/Biopolymer Facility and resulted in 6 fragments. The information obtained by microsequencing each of these 6 internal fragments is also shown in FIG. 6.

Search of peptide sequence databases revealed nothing contradicting that CAI is novel. The amino terminal fragment of CAI has limited homology to two partial protein sequences in the GenBank database. One is a membrane-bound form of [Fe]-hydrogenase from *Desulfovibrio desulficans* that was recently submitted directly to GenBank (FIG. 7). The other is a peptide that was purified by dissolution of a human kidney stone and separation of the resulting matrix proteins by 2-dimensional electrophoresis (urinary trace stone matrix protein, FIG. 7). Urinary stone matrix protein may be a common constituent of human kidney stones since similar peptides were visualized on gels prepared from the matrix of 3 additional urinary stones.

Together, these 2 homologies support the conclusion that CAI is a membrane-bound protein constitutively released into BSC-1 cell conditioned medium. No significant homology was uncovered between the 5 other CAI fragments and protein sequences in the database.

If released into tubular fluid by epithelial cells, CAI is expected to bind to freshly nucleated calcium oxalate crystals and become incorporated into the matrix of human kidney stones. CAI is a constituent of human urine that could adhere to crystals, thereby protecting the nephron against crystal retention and subsequent nephrolithiasis. Initially the method described herein utilizing affinity to COM crystals as a purification tool yielded a band on a PVDF blot ($M_r$ 57,000 Da) that when excised and subjected to N-terminal sequencing yielded uropontin (osteopontin) which was found to act similarly to CAI, that is blocking adhesion of COM crystals to BSC-1 cells. This result confirms the general utility of this methodological approach to search for renal cell proteins that protect cells against adhesion of COM crystals.

4. Antibodies to CAI

CAI or fragments thereof purified from conditioned medium of BSC-1 cells is used to prepare a monospecific antibody as follows:

In general, CAI is emulsified with Freund's complete adjuvant and injected subcutaneously to immunize female New Zealand White rabbits. Two weeks later a booster injection of CAI in Freund's incomplete adjuvant is administered followed by four more booster doses injected at 3-week intervals thereafter. The rabbit is bled seven days after the last injection and the serum is separated by centrifugation. The immunoglobin G (IgG) fraction of the polyclonal rabbit antiserum raised against CAI is then separated by protein A-agarose affinity chromatography using Affi-Gel Protein A. A CAI-affinity support is constructed by coupling CAI to Affi-Gel, or by a novel method reported (Aithal, et al. 1988 and 1994). Briefly, a limited number of sulfhydryl groups are introduced onto the CAI by reaction with 2-iminothiolane (Pierce Chemical, Rockford, Ill.). The CAI-affinity support is constructed by linking amino groups on an AH-Sepharose 4B matrix (Pharmacia, Piscataway, N.J.) to sulfhydryl groups on the ligand using m-maleimidobenzoyl sulfosuccinimide ester (Sulfo-MBS, Pierce). The monospecific antibody is purified by passing the total IgG through the CAI-affinity support and then eluting the bound protein. The eluted IgG can also be used to prepare an antibody-affinity column utilizing the same method.

Monospecific Antibodies Against Fragments of the Crystal Adhesion Inhibitor Protein a. Preparation of Peptide Antigens and Rabbit Antisera Amino acid sequence information in FIG. 6 was used to prepare synthetic peptides for use as antigens to generate polyclonal antibodies to CAI. The sequence of the $NH_2$-terminal 16 amino acids and of a 13 amino acid-peptide internal fragment were each used to prepare a synthetic peptide at The University of Chicago Protein-Peptide Core Facility. The potential antigenicity (hydrophilicity) of the 7 different peptides was compared by using computer software programs based on algorithms to choose the optimal antigenic sequence for synthesis. Each of the two peptides chosen was linked to its own branched polylysine backbone thereby increasing its size in a Multiple Antigenic Peptide System (MAPS). (Posnelt et al. 1988) These "MAPS-proteins" were used as distinct antigens to immunize rabbits (Pocono Rabbit Farm and Laboratory, Inc., Canadenesis, Pa.). Each antibody reacted strongly against the MAPS-protein antigen that elicited it when evaluated in an enzyme-linked immunoabsorbant assay (ELISA).

b. Preparation of CAI Monospecific Antisera

Because each immune sera reacted strongly against the MAPS peptide used to generate it, the cognate MAPS peptide was employed as an antigen to prepare affinity-pure antisera from its respective sera. The affinity-purified, monospecific antisera recognized the intact CAI molecule. The MAPS peptides were coupled to ECH Sepharose 4B beads (Pharmacia) in carbodimide at pH 4.5 overnight. MAPS antigen columns were prepared, equilibrated with 10 mm Tris, pH 7.5, and a solution of the antibody diluted 1:10 in 10 mM Tris (pH 7.5) was passed over the column three times. The columns were washed with 10 mM Tris, pH 7.5, then 10 mM Tris, pH 7.5 plus 0.5 M NaCl, and finally eluted with 10 mM glycine pH 2.5. Antibodies were precipitated with ammonium sulfate, and dialyzed against PBS. Each of these monospecific antibodies recognized a single protein band whose apparent size was $M_r$ 39,000 when proteins in partially-purified conditioned medium from BSC-1 cells were separated by SDS-PAGE and the gels were blotted and probed.

Cell protein extracts were prepared by rinsing a monolayer of BSC-1 cells with PBS containing PMSF (1 mM) and aprotinin (0.15 U/ml) and then lysing the cells in 2% SDS containing 5% $-mercaptoethanol and 1 mM PMSF. Total cell proteins were separated by SDS-PAGE, electroblotted, and probed with each monospecific antibody against peptide fragments of CAI. Each of the antibodies recognized a band of $M_r$ 39,000 Da in the total cell extract, which appears to represent a cell-associated from of the protein. A second band of higher $M_r$ (49,000 Da) was also recognized and is possibly a more extensively glycosylated isoform.

A Western blot of partially-purified CAI probed with antibodies raised against MAPS peptides of CAI was prepared. Pooled fractions containing crystal-aggregating activity from a Biogel sizing column were combined, concentrated and rinsed with a Centricon-30 microconcentrator and separated by sodium dodecylsulfate-polyacrylamide gel electrophoresis (SDS-PAGE). The gels were blotted and probed with each of the two monospecific antibodies generated against MAPS peptides of CAI. Sequences used to prepare the different MAPS-peptide antigens were as follows:

Antibody used in Panel A directed against synthetic aeptide: $NH_2$-terminal 16 amino acids:

NH2-Lys-lle-Asn-Gly-Gly-Gly-Ala-Thr-Leu-Pro-Gln-Pro-Leu-Tyr-Gln-Thr-COOH  (SEQ ID NO:2)

Antibody used in Panel B directed against synthetic peptide: 13 amino acid-peptide internal fragment:

NH2-Leu-Asn-Asn-Asp-Tyr-Ser-Gln-Phe-Gly-Thr-Gly-Thr-Lys-COOH  (SEQ ID NO:3)

5. Isolation of a cDNA Encoding CAI

Isolation of a cDNA clone is sought initially by screening a renal epithelial cell cDNA library. The $NH_2$-terminal amino acid sequence of the CAI is used to generate oligonucleotide probes (20 mers) to screen a BSC-1 cell cDNA library in lambda gtI0. Positive clones obtained thereby are sequenced to yield the nucleotide sequence of the CAI and predict its full-length amino acid sequence. Alternatively, a monospecific antibody is used to screen a BSC-1 cell cDNA library in lambda gtI1 and the nucleotide sequence of positive clones is used to define the amino acid sequence of CAI.

Expression of the cDNA in an appropriate vector and cell line is used to prepare large quantities of the protein that is glycosylated as required for biological function. Isolation of a human cDNA clone and development of a polyclonal antibody that recognizes human CAI provide powerful tools for the diagnosis and treatment of patients with nephrolithiasis.

Obtaining a Full Length cDNA Clone Encoding the Crystal Adhesion Inhibitor a. Polymerase Chain Reaction (PCR) Strategy The amino acid sequence is now available for the amino terminus of CAI and for 6 fragments generated by lys-C protease cleavage (a total of 124 amino acids, FIG. 6). The amino terminus (33 total, 28 definite) and fragment #1 (31 total, 27 definite) are the longest regions of the peptide sequenced to date. PCR strategy to obtain the DNA sequence encoding either of the largest fragments is the preferred initial strategy because the expected PCR products are of a known size, although not too small to be detected and sequenced.

Utilizing the amino acid sequence information, degenerate oligonucleotide primers are prepared on an ABI automated oligonucleotide synthesizer. Regions on the 5' (sense) and 3' (antisense) region of each fragment are selected to allow preparation of primers 15 to 20 base pairs in length with the lowest degree of degeneracy possible. These primers are utilized to amplify BSC-1 cDNA by PCR. The cDNA is prepared utilizing the First Strand cDNA kit (Clonetech, Palo Alto, Calif.) or RNA isolated from BSC-1 cells with the TRIzol reagent (Gibco BRL, Grand Island, N.Y.) using both random hexamer and oligo dT primers. Cells that are quiescent for 2 days are used to prepare RNA, because maximal levels of CAI are present in CM on day 3 of quiescence. The PCR reactions (100 $\mu$l) contain 0.2 $\mu$M each of dATP, dCTP, dGTP, dTTP (Boerhinger Mannheim); 3.75 ng/$\mu$l cDNA; 0.2 $\mu$M sense and antisense primers; 125 mU Taq polymerase (Boerhinger Mannheim); and 1×Taq polymerase buffer (supplied with enzyme). PCR products (5 $\mu$l) analyzed by agarose gel electrophoresis (4% NuSieve, FMC, Rockland, Me.) for products of the predicted size for each primer pair (56 to 99 base pairs). DNA in bands of the sought-after size cut from the gels and used as a template for reamplification with each individual primer alone, as well as both together. Those bands that amplify only with both primers together are chosen for further analysis.

For sequencing, PCR products (50–75 $\mu$l) are analyzed on a low melting point gel (2% Sea Plaque Agarose, FMC). The band of interest is excised and placed in Sea Plaque elution buffer (0.3 M NaCl, 20 mM Tris, pH 7.5, 0.1% SDS) at 65° C. for 10 minutes. DNA is extracted twice with phenol/chloroform/iso amyl alcohol, precipitated with ethanol, and ligated into the pGEM-T Vector (Promega, Madison, Wis.) with T4 DNA ligase (Takara DNA Ligation Kit, Painvera Corp., Madison, Wis.). DH5α™-competent cells (GibcoBRL, Gaithersburg, Md.) are transformed with the ligated vector, plated onto LB agarose plates containing ampicillin and 2% X-galactose, and incubated overnight to amplify the plasmids. Single positive colonies are selected (up to 8 from each plate), grown in Terrific Broth containing ampicillin, (Tartof et al. 1988) and plasmids isolated utilizing the QiaPrep 8 Plasmid Kit (Qiagen, Chadworth, Calif.). An aliquot of each plasmid is digested with the Sph 1 and Pst 1 restriction enzymes (Promega) and analyzed on an agarose gel. For those plasmids containing inserts, the remaining DNA is sequenced by Dye Terminator Cycle Sequencing (DNA Sequencing Kit, Perkin Elmer, Foster City, Calif.), utilizing an ABI Prism 377 DNA Sequencer by priming with the SP6 or T7 promoters (New England BioLabs, Beverly, Ma.) contained in the pGEM-T vector. For each fragment of DNA sequenced, the amino acid sequence encoded by the fragments of DNA sequenced is computed in all three reading frames, sense and antisense, with MacVector software (Oxford Molecular Group, Great Britain) and compared to the amino acid sequence of the CAI fragment under study. DNA fragments that do not encode CAI are not studied further.

After the DNA sequence encoding a fragment of the CAI peptide is available, a nondegenerate oligonucleotide probe is prepared and radiolabelled with T4 kinase (New England BioLabs) and [$^{32}$P]dATP. The radiolabelled probe is used to screen one or more kidney cDNA libraries. Available libraries include three BSC-1 cDNA libraries previously prepared by Clonetech, two in λgt10 and one in λgt11, as well as a human kidney cDNA library in λgt10 from Dr. Graham Bell. Initially, a BSC-1 cDNA library in λgt10 is titred in LE 392 competent E. coli cells. After the phage titre is determined, 12 top agarose and agarose plates (150-mm) with approximately 40,000 plaques each are prepared to allow screening of approximately $5 \times 10^5$ clones. Nitrocellulose membranes (0.45-μm, Schleicher and Schuell, Keene, N.H.) are placed atop the plates for 1 minutes to lift plaques, then denatured for 1 minute in 0.5 N NaOH/3 M NaCl, neutralized twice for 1 minute each in 0.5 M Tris/1.5 M NaCl, incubated for an additional minute in 20×SSC (0.3M Na Citrate, 3M NaCl), and dried at 80° C. in a vacuum oven for 2 hours.

Filters are hybridized with the radiolabelled pirobe encoding a portion of the CAI molecule. After prehybridization for 1 hour at 42° C. in 4×SSC (0.04 M NaPO$_4$, 2×Denhardt's buffer, 0.1% SDS, 100 μg/ml ssDNA, pH 6.5), the probe is added for overnight hybridization. Filters are successively washed 3 times (10 min each) in low-stringency wash buffer (2×SSC, 0.1% SDS) at room temperature, followed by 2 washes (15 min) in high-stringency wash buffer (0.2×SSC, 0.1% SDS) at 37° C. If excessive background radioactivity is detected, the wash is repeated at 42° C., and again at higher temperatures if necessary. Autoradiographs are prepared and the positive clones are identified on the appropriate plates.

For secondary screening, the large end of a Pasteur pipette is used to produce a plug in the top agarose in the region of positive hybridization. The plug is incubated in 1 ml of lambda dilution buffer (5.8 mg/ml NaCl, 2 mg/ml MgSO$_4$, 0.01% gelatin, 50 mM Tris, pH 7.4) with 1 drop of chloroform for 6 hours at 37° C. The phage titre is determined as above, and 5 plates with ~500 phages each are made. After overnight growth, nitrocellulose filters are prepared as above and screened with the oligonucleotide probe. The clone hybridizing most strongly is selected for tertiary screening. If all the plaques produced during tertiary screening are positive, a single one is chosen for further analysis. If not, another round of screening is performed until all the resulting plaques are positive.

A plug from the final positive plaque is incubated in 1 ml of lambda dilution buffer (5.8 mg/ml NaCl, 2 mg/ml MgSO$_4$, 0.01% gelatin, 50 mM Tris, pH 7.4) with 1 drop of chloroform for 6 hours at 37° C. The phage titre is determined as above. One top agarose and agarose plate is prepared with LE 392 cells and approximately $4 \times 10^4$ phages (near confluency). After 5–7 hours of growth, 10 ml of lambda dilution buffer is added and incubated at 4° C. overnight. The next day, a few drops of chloroform are added to the plates which are swirled and the liquid is poured into a 50 ml tube, 2 ml of chloroform is added, the tube centrifuged at 7200 g for 10 min, and the supernatant is saved. This high-tire phage stock (>$10^{10}$ pfu/ml) is titred and 700 μl is placed in a sterile Eppendorf tube with DNAase I (1 μl of 1 mg/ml) and heat-inactivated Rnase A (1 μl of 1 mg/ml) for 30 min at 37° C. The phage is precipitated with 700 μl of lambda PEG solution (20% PEG 6000, 2.5 M sodium acetate, pH 6.0) for one hour on ice, centrifuged, and the pellet resuspended in lambda dilution buffer. The resulting pellet is dissolved in 5 μl of 10% SDS and 0.5 μl of 0.5 M Na EDTA for 15 min at 65° C., extracted with phenol, then phenol chloroform, and the DNA is precipitated with sodium acetate and isopropanol.

An aliquot of the phage DNA is digested with the EcoR1 restriction enzyme (Promega) and analyzed on an agarose gel for the presence of an insert. After an insert is confirmed, it is sequenced by Dye Terminator Cycle Sequencing on an ABI Prism 377 DNA Sequencer as described above by priming with the 5' and 3' insert screening amplifiers present in the phage. The amino acid sequence encoded by the sequenced DNA is computed in all three reading frames, sense and antisense, with MacVector software, and compared to the amino acid sequence of the CAI fragments to confirm the predicted length and sequence of the clone.

If the PCR strategy is not successful, the conditions of the amplification and templates are systematically modified. Initially, the annealing temperature is varied between 45 to 60° C. Reactions are conducted in the presence of glycerol (10%) or DMSO (5%), or are initiated with all reagents at 4° C. ("cold start"), or after an initial denaturing step (95° C. for 5 minutes) before addition of Taq polymerase. Diverse templates are screened including CDNA prepared from BSC-1 cells that are growing, 1 day, or 3 days quiescent. DNA from the available libraries (3 BSC-1 cell libraries, 1 human kidney library, see above) is also used as a template. In addition, RNA from diverse sources (including human fetal liver, Clonetech) is used to prepare cDNA. This strategy is employed because although CAI has been isolated from kidney cells, the gene encoding it may be expressed to a greater extent in other organs.

If PCR utilizing primer pairs form the two ends of each of the 7 fragments does not easily yield the DNA sequence encoding one of the individual fragments. PCR primer pairs from different fragments may be tried. This is a less desirable strategy because the size of the sought-after DNA fragment is not known. Pairs of primers are prepared from each of the 7 fragments. PCR products generated by primers derived from 2 different peptide fragments that yield strong bands are cut from the gels. Each is used as a template for reamplification with an individual primer alone, as well as both together. Those bands that amplify only with both primers together are chosen for further analysis. Southern blots of the PCR products are prepared. PCR primers prepared for each of the CAI fragments other than the two used in the PCR reaction (5 total) are radiolabelled with T4 kinase (New England BioLabs) and [$^{32}$P]dATP, and used to probe the Southern blot. Bands that hybridize with this mixture of probes have a higher probability of being the sought-after one because they contain the DNA sequence encoding other fragments of CAI. These candidate DNA fragments are sequenced by amplification in the pGEM-T vector and competent E. coli cells, followed by Dye Terminator Cycle Sequencing as described above. If it is confirmed that the DNA sequence produced by PCR encodes CAI, this information is used to prepare nondegenerate probes to screen a cDNA library in λt10 to obtain a full-length clone as described above.

b. Preparation of Additional CAI for Amino Acid Microsequencing

If the PCR strategy outlined above does not readily yield the DNA sequence encoding a fragment of CAI, additional protein may be prepared for cleavage and microsequencing to supplement amino terminus and 6 internal fragments already sequenced. Amino acid sequencing of new cleavage fragments might identify a fragment that connects 2 of the existing fragments, allowing design of primers that bracket a much larger sequence of known size. Regions of the protein encoded by less degenerate sequences (i.e., containing methionine and tryptophan residues) might also be identified.

To prepare additional CAI protein, BSC-1 cells are grown in Dulbecco-Vogt modified Eagle's medium containing 25 mM glucose (DMEM), 1.6 µlM biotin and 1% calf serum at 38° C. in a $CO_2$ incubator. Under these conditions, BSC-1 cells achieve confluence at $10^6$ cells per 60-mm plastic plate (Nunc). High-density, quiescent cultures are prepared by plating 2×1 cells in a 60-mm dish. The spent medium is changed after 3 days so that there are $3-4\times10^6$ cells/plate 6 days later. Medium is aspirated and replaced with fresh medium containing 16 µM biotin and 0.01% calf serum; 3 days later the quiescent medium is harvested for isolation of CAI.

To isolate CAI protein, quiescent medium is passed through a 0.22-µm filter to remove any cells or debris. The conditioned medium is subjected to ultrafiltration through a YM 30 membrane (Amicon) to eliminate molecules with an apparent $M_r$ of <30,000. The filtrate is loaded onto a DEAE Sepharose anion-exchange column (Pharmacia) and eluted with 0.4 M NaCl. Na EDTA is added to the eluate to achieve a final concentration of 50 mM. Two days later the eluate is applied to a Biogel A 0.5 M column (100–200 mesh, 1.5×90 cm) equilibrated with 10 mM Tris containing 40 mM choline chloride at pH 7.4. The column is eluted at 4° C. with the same buffer at a flow rate of 15 ml/hr, and 3 ml fractions are collected. Fractions are assayed for crystal adhesion-inhibitory activity which elutes at an apparent molecular weight of ~15,000 Da under these conditions. Active fractions are pooled, concentrated with a Centricon-30 microconcentrator (Amicon), analyzed in 20% acrylamide by SDS-PAGE, and electroblotted at 20V overnight in 10 mM CAPS and 10% methanol onto an Imobilon-PSQ membrane. The blots are stained with amido black, and the predominant band at $M_r$ 39,000 Da is excised and submitted, for example to the Rockefeller University Protein Sequencing/ Biopolymer Facility, for cleavage and microsequencing. Any additional sequence information obtained is utilized to design new degenerate primers for PCR.

c. Screening of a cDNA Library with Degenerate Nucleotide Probes

If the PCR strategy does not yield the DNA sequence encoding a fragment of CAI, another potential strategy is to screen an available BSC-1 cDNA library with a single long degenerate probe prepared using the amino acid sequence information contained in one of the 7 peptide fragments in FIG. 6. This strategy is only utilized if the PCR strategy is not successful.

A peptide fragment is selected to allow preparation of a DNA probe of no less than 20 base pairs in length with the lowest degree of degeneracy possible, and then radiolabelled with T4 kinase and [$^{32}$P]dATP. One of the BSC-1 cDNA libraries in λgt10 is titred, plated out in LE 392 cells, and duplicate nitrocellulosse filters are prepared from each plate. The filters are initially probed with the longest radiolabelled probe possible (30–50 base pairs) with the lowest degree of degeneracy possible. Initial hybridization and wash temperatures are selected based on the length of probe utilized, and subsequently adjusted based on the amount of background. Duplicate filters prepared from plates with positive plaques are examined to eliminate artifact, and plaques that hybridize with the probe on both filters are selected for secondary screening, and a positive plaque selected for tertiary screening. If all the plaques produced during tertiary screening hybridize with the probe, a single one is chosen for further arialysis. If not, another round of screening is performed until all the resulting plaques are positive. A plug from the final positive plaque is isolated, amplified in LE 392 cells, and the phage DNA isolated as described above for sequencing. If an insert is confirmed, it is sequenced by Dye Terminator Cycle Sequencing and the amino acid sequence encoded by the sequenced DNA is computed in all three reading frames, sense and antisense, with MacVector software, and compared to the amino acid sequence of the CAI fragments to confirm the predicted identity of the clone.

If the initial hybridization in a NaCl/Na citrate (SSC) buffer produces a large number of positive clones, screening in a tetramethylammonium chloride (TMAC)-containing buffer is also performed, since hybridization of probes with DNA sequences in TMAC is dependent on temperature alone and relatively independent of the G-C content, reducing background. If screening with a degenerate probe is unsuccessful, screening with a single non-degenerate probe (30–50 base pairs) based on codon usage frequencies is also useful.

d. Screening of a cDNA Library with Monospecific Antibodies

Two monospecific antibodies, one against the amino-terminal fragment and one against one of the internal fragments are aspects of the present invention. They are useful to screen a BSC-1 library in λgt11 if the PCR strategy is not initially successful. This library has an amplified titer of 24 $10^9$ pfu/ml ($1.0\times10^7$ pfu/ml unamplified). This library contains an estimated $4\times10^6$ independent clones with an average insert size of 1.6 kb (range 0.2–4.0 kb). The library is titred and plated out in Y1090r cells, and nitrocellulose filters are prepared from each plate. The filters are probed with one of the monospecific antibodies followed by biotinylated antirabbit IgG, and detected with avidin-horseradish peroxidase complex followed by peroxidase substrate (4-chloro-1-naphthol, imidazole, and hydrogen peroxide). A plaque that hybridizes most strongly is selected for secondary screening with the other monospecific antibody. The plaque that hybridizes most strongly during secondary screening with the second antibody is selected for tertiary screening with the first antibody. If all the plaques produced during tertiary screening hybridize with the first antibody, a single one is chosen for further analysis. If not, another round of screening is performed until all the resulting plaques are positive. A plug of the final positive plaque is isolated, amplified in Y1090r cells, and the phage DNA isolated for sequencing as described above. If an insert is confirmed, it is sequenced by Dye Terminator Cycle Sequencing, and the amino acid sequence encoded by the sequenced DNA is computed in all three reading frames, sense and antisense, with MacVector software, and compared to the amino acid sequence of the CAI fragments to confirm the correct identity of the clone.

If one, but not both antibodies recognize a given fusion protein of CAI produced by Y1090r cells, each of the individual antibodies is used separately during primary, secondary, and tertiary screening of the library. If screening with neither antibody is successful, production of an antibody to native CAI ($M_r$ 39,000 Da) or a synthetic fusion protein is undertaken.

Other Inhibitors of COM Crystal Adhesion and Endocytosis

Other inhibitors of COM rystal adhesion are known but none are proposed for clinical use to prevent stone disease. Adhesion of COM crystals to cells was blocked by the polyanion, heparin, a glycosaminoglycan. Other glycosaminoglycans including chondroitin sulfate A or B, heparan sulfate and hyaluronic acid, but not chondroitin sulfate C prevented binding of COM crystals. Two nonsulfated polyanions, polyglutamic acid and polyaspartic acid, also blocked adherence of COM crystals. Three molecules found in urine, nephrocalcin, uropontin, and citrate each inhibited binding of COM crystals, whereas urinary Tamm-Horsfall glycoprotein did not. Prior exposure of crystals but not cells to inhibitory molecules blocked adhesion suggesting that these agents exert their effect at the crystal surface. Inhibition of crystal binding followed a linear Langmuir adsorption isotherm for each inhibitor identified, suggesting that these molecules bind to a single class of sites on the crystal that are important for adhesion to the cell surface. Inhibition of crystal adhesion by heparin was rapidly overcome by the polycation protamine, suggesting that the glycosaminoglycan regulates cell-crystal interactions in a potentially reversible manner.

There are other inhibitors of COM crystal adhesion and/or uptake that can be distinguished from CAI. Fibronectin, a component of the ECM, contains an RGD sequence which mediates binding of the protein to a plasma membrane integrin fibronectin receptor. The recognition sequence RGD is an important mediator for the interaction cell surface receptors (integrins) and ECM proteins. Because the RGDS peptide and the protein fibronectin each inhibit COM endocytosis, crystal engulfment by the cell may involve participation of the fibronectin receptor. The α3, αv, and β1 integrin subunits which can serve as components of the fibronectin receptor have recently been demonstrated on the surface of BSC-1 cells by immunofluorescence microscopy. After exposure of cells to a metabolic stress (e.g., $H_2O_2$) the quantity of α3 staining on the apical cell surface increased, suggesting that stress could increase the number of fibronectin receptors on the cell, and possibly increase crystal uptake as well.

THP is the most abundant protein in human urine, although its role in renal physiology remains uncertain. The glycoprotein is synthesized in the thick ascending limb of the loop of Henle (TALH) and early distal tubule. The protein is anchored to cell-surface lipids by a phospholipase C-sensitive linkage from which it is cleaved and released into tubular fluid. THP is a potent inhibitor of COM crystal growth and aggregation in vitro, and is a ligand for specific cytokines such as tumor necrosis factor and interleukin-1. THP has been proposed as a defense against bacterial adhesion and colonization, and to maintain water impermeability of the TALH. THP inhibits COM endocytosis in monkey kidney epithelial cells by acting on cells, not by coating the crystals. Because THP contains an RGD sequence and RGDS decreased crystal endocytosis, it is possible that the glycoprotein inhibits COM crystal uptake by blocking access of the crystal to a cell surface integrin fibronectin receptor. Alternatively, THP could exert its biological effect on tubular cells by other mechanisms. Tubular fluid may be supersaturated as early as the bend of Henle's loop which favors the formation of crystals. Thus THP synthesized in the TALH and present in fluid of the distal nephron might prevent cells from engulfing COM crystals as they flow downstream. Two additional agents that possess different biological properties also inhibit COM crystal endocytosis: heparin and TGF-β2.

Figure 4:
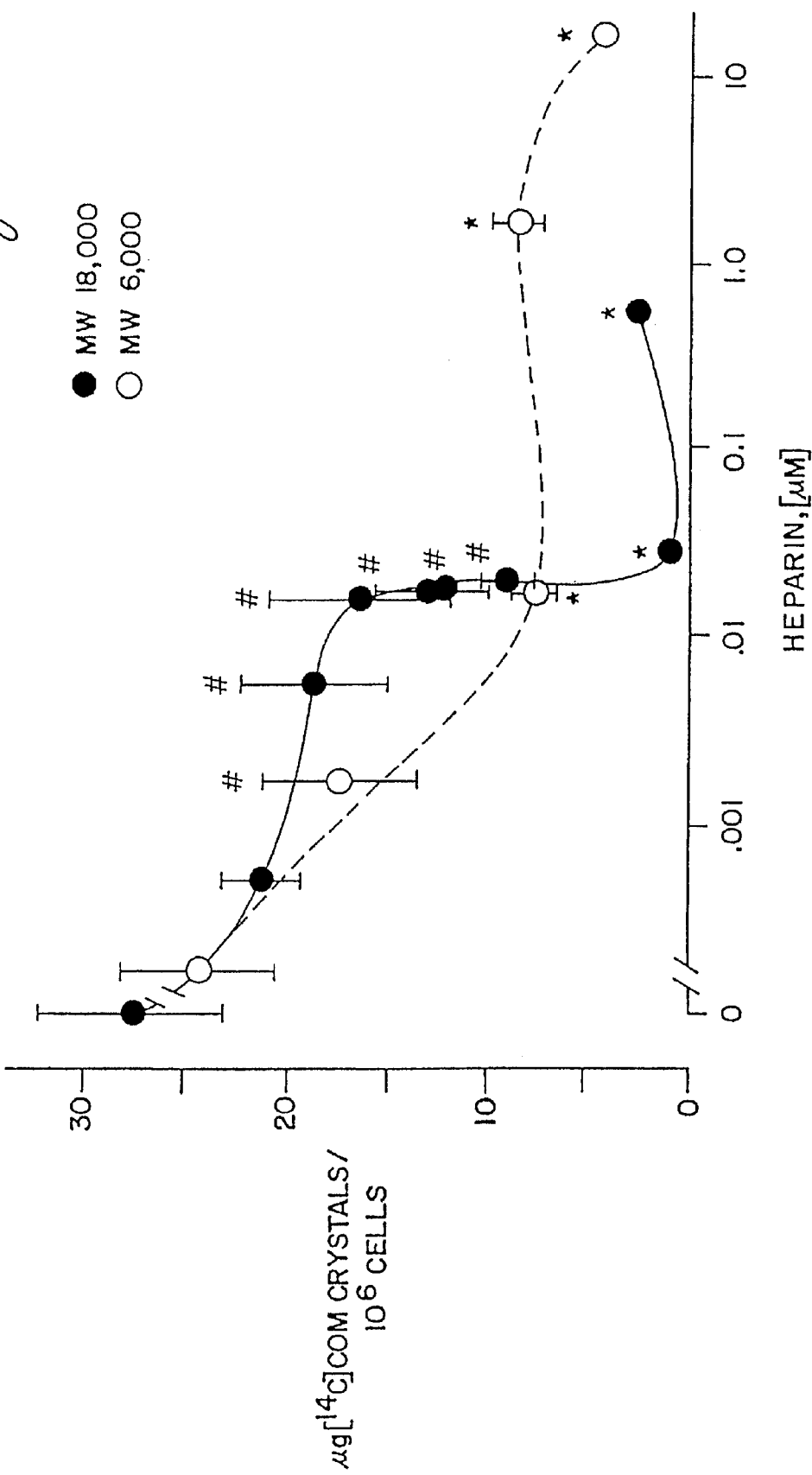
FIG. 4 shows inhibition of COM crystal adhesion to BSC-1 cells by heparin.
Figure 5:
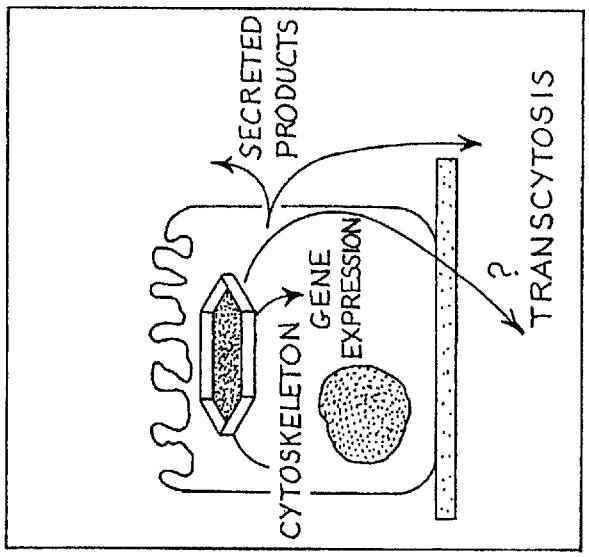
FIG. 5 presents sequential events in the interaction between COM crystals and renal epithelial cells that may result in nephrolithiases A. Adhesion, B. Internalization, and C. Cellular Responses.
Figure 5:
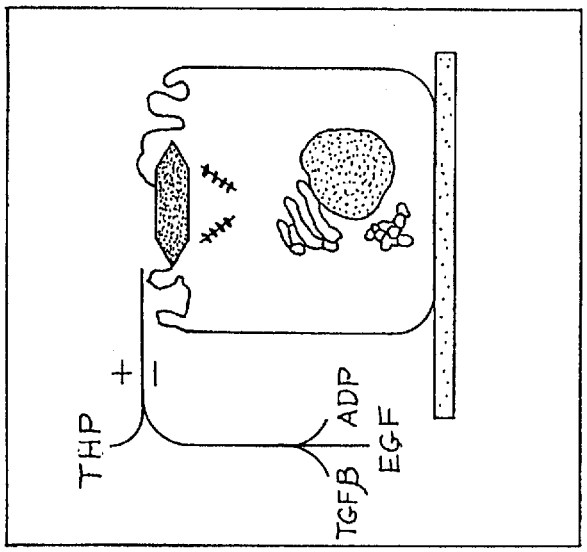
Figure 5:
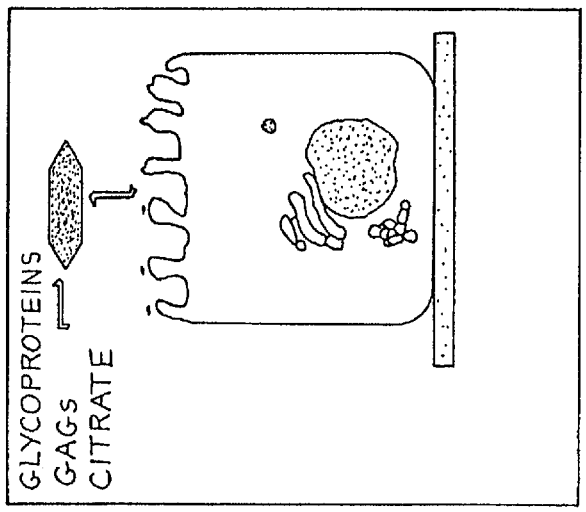

FIG. 4 shows inhibition of COM crystal binding to BSC-1 cells by heparin. High-density, quiescent cultures were prepared, the medium was aspirated and replaced with PBS containing specified concentrations of heparin. [$^{14}$C]COM crystals were added (200 μg/ml) and 2 minutes later the buffer was removed, the cell layer was rinsed three times, and cell-associated radioactivity was measured. ($P<0.05$, $P<0.001$ compared to control.) Heparin is a potent inhibitor of COM crystal growth, and blocks endocytosis of COM crystals by BSC-1 cells. At a concentration as low as 0.006 μM, heparin (18,000 Da, closed circles) decreased adherence of COM crystals by 33% ($P<0.05$) (FIG. 4). Maximal inhibition (95%) was observed at concentrations above 0.028 μM ($P<0.001$). Heparins of lower molecular weight (6,000 daltons, open circles) and 3,000 daltons also inhibited COM crystal adhesion but were not as effective as the larger compound (18,000 daltons) on a molar basis. Individual subunits of the heparin molecule were assessed for their capacity to inhibit binding of COM crystals. Neither D-glucuronic acid, D-glucosamine, D-glucosamine 2 sulfate, D-glucosamine 3 sulfate, D-glucosamine 6 sulfate, D-glucosamine 2,3 disulfate, D-glucosamine 2,6 disulfate, nor six different heparin disaccharides (III-A, IV-A, I-S, II-S, III-S, IV-S) altered COM crystal adhesion, suggesting that more than two repeating units of the glycosaminoglycan are required for an inhibitory effect. Adhesion of COM crystals to MDCK cells was inhibited maximally (89%) by 0.55 μM heparin ($P<0.001$). Heparin (0.55 μM) also decreased adhesion of COM crystals (200 μg/ml) to 3T3 fibroblasts by 85% ($P<0.001$) demonstrating that its inhibitory effect is not specific for epithelial cells.

The capacity of sulfate-containing glycosaminoglycans ordinarily found in human urine to alter adherence of COM crystals was investigated. Chondroitin sulfates A and B each inhibited COM crystal adherence when present at concentrations above 1.4 μM and 0.4 μM, respectively ($P<0.05$), whereas concentrations of chondroitin sulfate C as high as 37 μM had no effect. Heparan sulfate at concentrations above 0.8 μM decreased crystal adherence, as did hyaluronic acid above 0.01 μM. Since 4 separate chondroitin sulfate disaccharides were without effect (0-S, 4-S, 6-S, Di-SB;), it appears as was the case for heparin, that more than 2 repeating units are required to inhibit crystal binding to cells. Thus, multiple sulfated and nonsulfated glycosaminoglycans can block COM crystal adherence, but not all members of this class of molecules can do so.

The effect of other charged molecules on adhesion of COM crystals, was evaluated. Polyaspartic and polyglutamic acid, which are each potent anionic inhibitors of COM crystal growth, blocked adhesion of COM crystals at concentrations above 0.007 μM and 0.02 μM, respectively ($P<0.001$). The cations polyarginine and polylysine, employed as control molecules, had no effect when present in concentrations as high as 1 μM. Therefore two nonsulfated polyanionic molecules inhibited binding of COM crystals to renal epithelial cells.

The effect of other sulfated and nonsulfated anions, some of which are present in urine, was studied. Pentosan polysulfate is a synthetic compound which is a potent inhibitor of COM crystal growth and can appear in urine when administered by the oral route. At concentrations above 0.33 μM, the compound inhibited COM crystal adherence ($P<0.001$). Polyvinyl sulfate and dextran sulfate, which are not found in urine, also blocked crystal binding at concentrations in excess of 0.1 μM and 0.01 μM, respectively. The polyanion citrate blocked adherence of COM crystals when present at concentrations above 250 μM, a value similar to that ordinarily present in human urine. Phosphocitrate, a synthetic derivative of citrate and a potent inhibitor of COM crystal growth blocked COM crystal adhesion at concentrations above 50 μM.

Nephrocalcin and uropontin are each potent inhibitors of COM crystal growth, whereas THP inhibits aggregation of these crystals. Nephrocalcin inhibited COM crystal adhesion at concentrations above 0.05 μM, with maximal inhibition of 84 of at 0.25 μM (P<0.001). Uropontin blocked COM crystal binding by 73% at a concentration of 0.1 μM (P<0.05); higher concentrations were not studied due to limited availability of the purified protein. THP had no effect on crystal adhesion. Of note, in the buffer system employed (Na 155 mM, pH 7.4, Ca 0), THP was unlikely to self aggregate. The concentration range of each protein studied was similar to that found in human urine.

A common feature of the molecules that inhibit COM crystal adhesion to cells is their polyanionic character. Sulfate (glycosaminoglycans, dextran sulfate, polyvinyl sulfate) and carboxyl groups (polyaspartate and polyglutamate) each appear to associate with the crystal and prevent the inhibitor-crystal complex from binding to the cell surface. The stereospecific presentation of negative charge on the molecule appears to be critical, because chondroitin sulfates A, B and C each contain sulfate moieties, but only A and B inhibit crystal adhesion. Because each of the effective molecules identified are anionic and appear to act directly on the crystal rather than the cell, it is likely that the site to which these inhibitors bind is cationic, for example calcium ions on the crystal surface. Furthermore, each of the adhesion inhibitors for which data is available (e.g., heparin, chondroitin sulfate A, chondroitin sulfate B, heparan sulfate, polyaspartate, polyglutamate, citrate, phosphocitrate, pentosan polysulfate, nephrocalcin, uropontin) also blocks growth of COM crystals. Thus sites on the crystal surface that are important for crystal growth and that mediate binding to the cell surface may be related or identical.

Reversibility of Heparin-mediated COM Crystal Adhesion Inhibition

To determine if inhibition of COM crystal adhesion to the cell surface is reversible the time course of heparin action was defined. COM crystals were added to the medium of high-density, quiescent cultures followed by addition of heparin (10 μg/ml, 0.55 μM) 1 to 30 minutes later. The quantity of adherent crystals was measured after 60 minutes. Adhesion of crystals to the monolayer appeared to stop immediately upon addition of heparin. This effect was independent of the duration of prior exposure of cells to crystals. Importantly, heparin did not appear to displace crystals already bound to cells, even when the polyanion was present for an additional 55 minutes.

The effect of protamine sulfate, a polycationic protein used to reverse the anticoagulant effects of heparin was studied. When added together with heparin (10 μg/ml), protamine sulfate (100 μg/ml) abolished the polyanion's inhibitory effect, whereas protamine sulfate alone was inert. Even after 30 minutes exposure to heparin, addition of protamine sulfate completely reversed inhibition of crystal binding by the glycosaminoglycan.

To compare the relative inhibitory capacity of each of the anions identified, the Langmuir-type isotherm plot was used to calculate a value for crystal adhesion in the presence of different concentrations of the inhibitor under study. In this analysis, the term B0/(Bo-Bcxp) is plotted against 1/[I] 1); "$B_0$" is the quantity of bound crystal in the absence of inhibitor, "$B_{exp}$" is the bound crystal with inhibitors present, and "I" indicates the concentration of inhibitory agent present. A linear Langmuir isotherm is consistent with the hypothesis that the inhibitor adsorbs to a single binding site effectively blocking adhesion of the crystal to the cell, and suggests that adhesion only occurs at uncoated sites. The slope of this line is termed the Langmuir affinity constant (dissociation constant) which provides an affinity index of a given molecule for the dissociation site. A lower value for the Langmuir affinity constant signifies greater affinity of the inhibitor for the dissociation site than does a higher one. For each of the anionic inhibitors identified, the Langmuir isotherm plot of crystal adhesion versus reciprocal of inhibitor concentration was linear. This result is consistent with the interpretation that inhibitory molecules bind to a single class of sites on the crystal surface that are crucial for adhesion to the cells, and that once these sites on the crystal are coated with inhibitory molecules, adhesion to the cell is blocked. Based on the calculated constants, hyaluronic acid, dextran sulfate, heparin, polyaspartic acid, polyglutamic acid, polyvinyl sulfate, uropontin and nephrocalcin have the greatest affinities for the presumed binding sites on the crystal surface that mediate adhesion to cells, with constants ranging from 0.013 μM (hyaluronic acid and dextran sulfate) to 0.107 μM (nephrocalcin) (Table 2). Also listed for comparison are the concentrations of each anion that inhibited crystal adhesion by 50%.

The reversible inhibition of crystal binding to renal epithelial cells by heparin is of particular interest. The presence of this molecule in the culture medium nearly abolishes crystal adhesion. When added after crystals, heparin can not displace those crystals already bound to cells, but does prevent adhesion of additional crystals. Although heparin is a potent inhibitor of crystal binding, its effect can be completely reversed by protamine, even when this cationic protein is added up to 30 minutes later. Because heparin appears to act directly on crystals rather than cells, it appears that this glycosaminoglycan binds reversibly to a site on the crystal surface. COM crystals adhere to two renal epithelial lines (MDCK and BSC-1) as well as to 3T3 fibroblasts. The adherence of COM crystals to all three cell lines is blocked by heparin so that the structural characteristics of the cell surface that mediate the interaction between the crystal and plasma membrane may be shared by diverse types of cells.

Coating of Crystals or Cells by Molecules That Block Adhesion of Crystals

Studies were performed to determine if inhibition of crystal adhesion by the specific molecules identified above was mediated by an interaction at the crystal andlor cell surface. Adhesion of crystals previously coated with heparin, chondroitin sulfate B, dextran sulfate, polyaspartate, polyglutamate, nephrocalcin, or uropontin was in each case less than control (P<0.001; P<0.05 for polyglutamate). Crystals coated with polyarginine, polylysine or albumin bound to cells to the same extent as did uncoated crystals. Binding of uncoated COM crystals to monolayers that had been exposed to the molecules under study did not differ from adhesion of crystals to uncoated cells. Thus the capacity of specific polyanions to inhibit adhesion of COM crystals to BSC-1 cells appears to be mediated by their ability to act on the crystalline surface.

Role of Filaments in Crystal Adhesion

Actin filaments are necessary for phagocytosis by nonrenal cell types such as macrophages. To determine if actin filaments were associated with the internalization of COM crystals phalloidin which selectively binds to F (filamentous)-actin but not G (globular)-actin was used. At one hour after exposure to COM crystals, increased phalloidin staining was apparent in a region of the cell just beneath the crystal; these changes were maximal at three hours. Phalloidin staining appeared to follow the outline of the crystal during engulfment, suggesting a role for actin during internalization.

Changes in other cytoskeletal filament systems were identified.

Staining of cells exposed to COM crystals with a monoclonal antibody to tubulin did not reveal any morphologic alterations. Previous studies revealed that some compounds which are mitogenic for BSC-1 cells caused surprisingly rapid alterations in the cytokeratin components of the intermediate filament network. The effect of COM crystals on cytoskeletal intermediate filaments was studied using a monoclonal antibody to cytokeratin 8. In control cells this protein stained most intensely in a perinuclear zone, but redistributed to a diffuse cytoplasmic fiber pattern 8 hours after exposure to COM crystals. Cytokeratin 8 relative fluorescence intensity was measured on 16 fields of 200 cells each. Mean relative fluorescence intensity was 14% above control at one hour ($P<0.01$), 93% after 3 hours ($P<0.001$), and maximally increased 336% above control 8 hours after addition of COM crystals ($P<0.001$). Cytokeratin 8 reorganization was observed in all cells after addition of COM crystals, and was not confined to those which internalized a crystal, suggesting that cell-to-cell communication had occurred in response to crystal uptake, perhaps via release of an autocrine factor.

The apparent intracellular location of COM crystals observed with the polarizing microscope was confirmed by electron microscopy. After 30 minutes many cells contained COM crystals in a peripheral location just under the plasma membrane. One hour after addition, crystals were often in a central location within cells. In many instances a membrane-like structure appeared to surround the crystal suggesting that it was within a vesicle. Thus endocytosis can occur as early as 30 minutes after exposure of cells to COM crystals.

COM Crystal Endocytosis in Different Types of Cells

To explore endocytosis of urinary crystals by other types of cells, COM, HA, or BR crystals (200 µg/ml) were added to high-density, quiescent cultures of MDCK cells or Balb/c3T3 fibroblasts. After one hour, 32% of MDCK cells endocytosed at least one COM crystal, whereas only 2% ($P<0.001$) internalized HA crystals, and 13% ($P<0.001$) endocytosed BR crystals. Balb/c3T3 fibroblasts engulfed each of the three crystals; COM crystals were endocytosed by 40% of the cells, HA crystals by 14% ($P<0.001$ compared to COM crystals), and BR crystals by 33% (P=NS compared to COM crystals). Fibroblasts engulf HA crystals (14%) to a greater extent than do BSC-1 cells (7%) or MDCK cells (2%), and also take up BR crystals (33%) more avidly than cells of the BSC-1 (3%) or MDCK (13%) lines.

Modulators of COM Crystal Endocytosis in BSC-1 Cells

High-density, quiescent cultures of BSC-1 cells were used to search for modulators of COM crystal endocytosis. Known mitogenic signals for BSC-1 cells were studied, including EGF and the nucleotide ADP which stimulate migration of these cells in wounded monolayer cultures. EGF (10 ng/ml) increased endocytosis 55% compared to control ($P<0.001$), and ADP (2 µM) enhanced crystal uptake 52% ($P<0.001$). Raising the calf serum concentration from 0.01% (control) to 0.1% augmented COM crystal endocytosis by 43% at one hour ($P<0.001$). Exposure to low-potassium (low-K) medium is mitogenic for BSC-1 cells and is associated with altered plasma membrane structure and function within 3 minutes. Substitution of a low-K medium for one hour augmented uptake of crystals by 20% compared to control medium,($P<0.01$), and after two hours by 23% ($P<0.05$). The stimulatory effects of ADP (200 µM) and EGF (5 ng/ml) were not additive.

Negative Regulation of COM Crystal Endocytosis in BSC-1 Cells

The tetrapeptide arginine-glycine-aspartic acid-serine (RGDS), heparin, and the negative autocrine growth factor secreted by BSC-1 cells, TGF-β2, have been found to inhibit migration of renal epithelial cells in wounded monolayer cultures. The biological effects of RGDS are apparently mediated by its binding to a cell surface integrin receptor. Agents which alter motility of renal epithelial cells were tested for modulation of endocytosis of particulates. RGDS at a concentration of 5 µg/ml inhibited COM crystal endocytosis by 30% compared to control ($P<0.001$), with maximal inhibition of 41% at higher concentrations. Because RGDS can bind to the integrin fibronectin receptor, the effect of this protein on crystal endocytosis was assessed. Fibronectin at a concentration of 2.5 µg/ml maximally inhibited COM crystal endocytosis by 33% ($P<0.01$).

Heparin (2 µg/ml) decreased COM crystal endocytosis 36% compared to control ($P<0.001$), and concentrations as high as 100 µg/ml did not inhibit uptake further. Heparan sulfate (2–25 µg/ml) did not alter endocytosis of COM crystals. TGF-β2 maximally decreased COM crystal endocytosis by 40% at 2 ng/ml ($P<0.001$). The inhibitory effects of RGDS (10 µg/ml), heparin (5 µg/ml) and TGF-β2 (2 ng/ml) were not additive. Neither RGDS (10 to 50 µg/ml) nor heparin (100 to 200 µg/ml) inhibited endocytosis of latex beads suggesting that uptake of the beads may be mediated by a pathway different from the one used by COM crystals. Alternatively, latex beads might possess a greater affinity for the surface of BSC-1 cells than do COM crystals, and if so uptake of beads might not be inhibited by RGDS or heparin under these experimental conditions.

Effect of Negative Regulators of Crystal Endocytosis on Different Types of Cells To determine if the effect of negative regulators of COM crystal endocytosis was cell-type specific, COM crystals (200 µg/ml) were added to high-density, quiescent cultures of MDCK cells or Balb/c3T3 fibroblasts. Fibronectin (10 µg/ml) or RGDS (10 µg/ml) inhibited COM crystal endocytosis by MDCK cells 59% or 48%, respectively ($P<0.001$), but did not alter crystal uptake by fibroblasts. Heparin inhibited endocytosis in both MDCK cells (60%, P<001) and fibroblasts (24%, $P<0.001$). Thus fibronectin and RGDS inhibit COM crystal endocytosis in each of two renal epithelial cell lines (BSC-1 and MDCK) but not fibroblasts, whereas heparin inhibits endocytosis in all three cell lines.

Effect of Tamm-Horsfall Glycoprotein on COM Crystal Endocytosis

The effect of THP on crystal endocytosis was investigated because this most abundant urinary protein is also a potent inhibitor of COM crystal aggregation. THP decreased COM crystal endocytosis by 21% at a concentration of $10^{-8}$ M ($P<0.005$) and by 34% at $5\times10-8$ M ($P<0.001$). The urinary crystal growth inhibitor nephrocalcin at concentrations as high as 10–6 M, and bovine serum albumin (BSA) at a concentration of $5\times10-8$ M did not alter COM crystal uptake under these conditions.

Effect of Crystal or Cell Coating by Specific Agents on COM Crystal Endocytosis

To determine whether specific molecules that inhibit COM crystal endocytosis act by coating crystals, or by binding to the cell surface, COM crystals (100 µg/ml) were incubated with BSA ($5\times10^{-8}$ M), heparin (2 µg/ml), fibronectin (5 µg/ml) or THP ($5\times10-8$ M) for 4 hours, collected by centrifugation, resuspended in water, and then added to high-density, quiescent cultures. Endocytosis of crystals coated with any of the 4 agents was similar to uptake of uncoated control crystals. COM crystals (100 μg/ml) incubated with THP ($5 \times 10^{-8}$ M) were also added directly to the cultures without centrifuging or resuspending them; this raised the concentration of THP in the medium to $6 \times 10^{-10}$M. Crystals under this condition were endocytosed to the same extent as uncoated crystals. This result eliminates the possibility that THP was washed off COM crystals by the experimental protocol and confirms that inhibition of endocytosis by the glycoprotein is not mediated by coating the crystals.

TABLE 2

Molecules that inhibit adhesion of COM crystals to BSC-1 cells

| Molecule | Langmuir affinity constant (dissociation constant) | Half-maximal concentration |
|---|---|---|
| Chondroitin sulfate A | 0.038 μM | 0.6 μM |
| Chondroitin sulfate B | 0.206 μM | 0.1 μM |
| Chondroitin sulfate C | N.I. | N.I. |
| Dextran sulfate | 0.013 μM | 0.01 μM |
| DNA | N.D. | 1.0 μg/ml |
| Heparan sulfate | 0.881 μM | 0.1 μM |
| Heparin | 0.043 μM | 0.015 μM |
| Heparin MW 6000 | 0.002 μM | 0.002 μM |
| Heparin MW 3000 | 0.002 μM | 0.002 μM |
| Hyaluronic acid | 0.013 μM | 0.02 μM |
| Nephrocalcin | 0.107 μM | 0.075 μM |
| Pentosan polysulfate | 0.131 μM | 0.02 μM |
| Phosphocitrate | 43.8 μM | 50 μM |
| Polyarginine | N.I. | N.I. |
| Polyaspartic acid | 0.023 μM | 0.007 μM |
| Polyglutamic acid | 0.026 μM | 0.01 μM |
| Polylysine | 3.54 μM | 2.5 μM |
| Polyvinyl sulfate | 0.049 μM | 0.02 μM |
| Sodium citrate | 430.7 μM | 200 μM |
| THP | N.I. | N.I. |
| Uropontin | 0.043 μM | 0.02 μM |

N.I.: noninhibitory; N.D.: not determined.

Calcium oxalate monohydrate crystals stimulate gene expression in renal epithelial cells. Primary or secondary hyperoxaluria is associated with calcium oxalate nephrolithiasis, interstitial fibrosis and progressive renal insufficiency. Monolayer cultures of nontransformed monkey kidney epithelial cells (BSC-1 line) and COM crystals were used as a model system to study cell responses to crystal interactions that might occur in nephrons of patients during periods of hyperoxaluria. To determine if COM crystals signal a change in gene expression, Northern blots were prepared from total renal cellular RNA after the cells were exposed to crystals.

Effect of COM Crystals on Gene Expression in BSC-1 Cells

Expression of immediate early genes (c-myc, EGR-I, c-jun, c-fos, and Nur-77) was investigated in cells exposed to COM crystals (200 μg/ml) for specified periods of time. RNA was extracted from the cells and Northern blots were prepared and hybridized with specific [a $^{32}$P]dCTP cDNA probes. The transcript for c-myc was induced as early as 15 minutes with maximal expression at one hour. The transcript for EGR-1 was induced by 30 minutes with maximal expression at 1 to 2 hours. Similarly, the transcript for Nur-77 was induced at two hours, and c-jun, (minimally expressed under control conditions), also showed a maximal increase at that time. The transcript for c-fos was not detected in control cells, nor was it induced by addition of crystals. GAPDH, an enzyme that mediates glycolytic metabolism, was constitutively expressed and was not altered by addition of crystals; it served to document equal loading of RNA in different lanes of Northern blots.

Northern analysis was then performed using [α-$^{32}$P] cDNA probes to study proteins that regulate the ECM composition. Plasminogen activator inhibitor-1 (PAI1) was expressed constitutively in cells as a double transcript (2.4 and 3.4 kb in size). In the presence of COM crystals the message increased maximally between two and six hours, and returned to the control level by 12 hours. When the same blot was hybridized with a probe for urokinase-type plasminogen activator (u-PA), constitutive expression of the gene was detected that did not change significantly following exposure of the cells to crystals.

Northern blot analysis of mRNA encoding PDGF-A and -B chains was performed. Three transcripts encoding PDGF-A chain (2.8 kb, 2.3 kb, and 1.8 kb) are expressed in control cells. Expression increased maximally between two to six hours after exposure to crystals, a time course similar to that observed for PAI-I. The gene encoding PDGF-B chain (c-sis), was constitutively expressed and changed little after exposure to crystals. Connective tissue growth factor (CTGF) is a cysteine-rich protein that exhibits PDGF-like biological and immunologic activities. Its transcript was not detected under control conditions, but was induced after one hour of exposure to crystals and thereafter was expressed continuously for up to 24 hours. Table 3 shows that six genes (left panel) which contribute to the composition and regulation of ECM were constitutively expressed by BSC-1 cells, but their expression was not altered by exposure to COM crystals. Nine genes (right panel) that could play a role in fibrogenesis and proliferation were not expressed in BSC-1 cells nor did crystals induce their expression.

Specificity of Gene Expression

To determine if the capacity of COM crystals to stimulate gene expression is crystal-type specific, the effect of two calcium-containing crystals, BR or HA, and a non-crystalline particulate, latex beads, were studied. Cells were exposed to each particulate (200 μg/ml) for specified periods of time, RNA was isolated, and Northern blots were prepared and probed with [α-$^{32}$P] PDGF-A chain cDNA. Only COM crystals induced gene expression.

To determine whether stimulation of PAI-1 gene expression by COM crystals was cell-type specific, experiments were performed using cultures of canine renal epithelial cells (MDCK line) and Balbl3T3 fibroblasts. High-density, quiescent MDCK or 3T3 cells were exposed to COM crystals (200 μg/ml) for one, three, six, twelve, or twenty-four hours. Northern blots were prepared using 80 μg of total cellular RNA and hybridized with [α32$_p$] PAI-1 cDNA. Induction of the PAI-1 transcript in MDCK cells was detected three hours after exposure to COM crystals, whereas expression in 3T3 fibroblasts was not detected under control conditions or in the presence of crystals. To evaluate cell-type specificity of COM crystal-induced early gene expression, MDCK cells or 3T3 fibroblasts were exposed to crystals (200 μg/ml) for one, three, six, twelve or twenty-four hours, and Northern blots (20 μg total RNA per lane) were prepared. The crystals stimulated expression of EGR-1 in MDCK cells (at 6 hours) but not in 3T3 fibroblasts.

These results suggest that the capacity of COM crystals to stimulate gene expression in renal epithelial cells is crystal- and cell-type specific.

TABLE 3

EFFECT OF COM CRYSTALS ON GENE EXPRESSION IN BSC-1 CELLS

| Constitutive Expression Not Altered | Not Expressed or Induced |
|---|---|
| Laminin | Stromelysin |
| Collagen | Collagenase |
| Fibronectin | Interleukin 1β, -1α, -6 |
| Transforming growth factor -β1, -β2 | gro |
| Heat shock protein -70 | Tissue-type plasminogen activator |
|  | Basic fibroblast growth factor |
|  | Acidic fibroblast growth factor |

COM crystals were added to cultures of high-density, quiescent cells and RNA was extracted at eight different times (0–24 hours) thereafter. Northern blots were prepared and hybridized with each of the [α-32P]cDNA probes listed.

In summary, the interaction of kidney epithelial cells with COM crystals alters expression of genes that encode three classes of proteins: transcriptional activators, a regulator of ECM, and growth factors, Activation of PAI-1 gene expression without a change in u-PA favors accumulation of ECM proteins, as does increased expression of PDGF and CTGF which could also stimulate fibroblast proliferation in a paracrine manner. These results suggest that COM crystal-mediated stimulation of specific genes in renal tubular cells may contribute to the development of interstitial fibrosis in hyperoxaluric states.

Mechanisms that mediate the pathologic changes in hyperoxaluric states that are associated with the formation of kidney stones and interstitial fibrosis were investigated as follows:

Monolayer cultures of nontransformed monkey kidney epithelial cells (BSC-1 line) and COM crystals were used as a model system to investigate the molecular events that ensue when a crystal interacts with a renal tubular cell. As interstitial fibrosis is characteristic of the renal injury associated with hyperoxaluria, genes which encode proteins that regulate the composition of the ECM were examined. The results indicate that the interaction between COM crystals and renal epithelial cells induces and stimulates expression of specific genes which could mediate interstitial fibrosis in patients with hyperoxaluria.

The results demonstrate that genes encoding diverse classes of proteins are activated in renal epithelial cells exposed to COM crystals. There is rapid and transient induction of c-myc, Egr-1 and Nur-77 transcripts which peak at one to two hours; enhanced expression of PAI-1 and PDGF-A chain at two to six hours; and induction of CTGF at one hour that persists for 24 hours following the cell-crystal interaction. These findings provide evidence that the most common crystal in renal stones, COM, can activate gene and protooncogene expression in kidney epithelial cells.

Cellular Origin of CAI

To eliminate the possibility that CAI was constituent of calf serum that had become adherent to BSC-1 cells and was released into the conditioned medium, evidence that suggests a cellular rather than serum origin of CAI is summarized below.

Fresh DMEM containing 0.01% calf serum does not inhibit COM crystal adhesion to BSC-1 cells as does CM with the same amount of serum. Activity is released from the cells after only 1–2 days of conditioning, and is maximal by 3 days. Increasing the amount of calf serum present in medium to 1% from 0.01% did not increase the amount of activity released. The amino acid sequence data from the amino terminal and 6 internal fragments does not bear any homology to known serum proteins. FIG. 7 In additional control experiments, DMEM containing 0.01% calf serum was incubated with COM crystals. The crystals were isolated, washed, and dissolved in EDTA using the same protocol initially used to isolate CAI. When the resulting proteins were analyzed by SDS-PAGE, no band was seen at $M_r$, 39,000. Finally, a quantity of calf serum equivalent to that found in 1 liter of conditioned medium was processed using the same procedure to isolate CAI from quiescent medium: DEAE anion-exchange chromatography, treatment with EDTA, and size-exclusion chromatography. Fractions from the sizing column corresponding to those in which CAI is isolated were analyzed by SDS-PAGE, electroblotted, and probed with the monospecific antibodies to the synthetic peptide fragments of CAI. No chemiluminescence signal was detected. However, on a Western blot of total BSC-1 cell protein a predominant band at $M_r$ 39,000 was detected. Therefore, the available evidence strongly supports the conclusion that CAI protein originates from cells, not serum.

EXAMPLES

Example 1

Use of CAI DNA Probes to Study Regulation of CAI Gene Expression in BSC-1 Cells

When the sequence of the gene encoding CAI is available, the regulation of CAI.gene expression in BSC-1 cells is analyzed.

Phage DNA obtained as described herein is digested with the EcoR1 restriction enzyme, and the DNA sequence encoding CAI is isolated by agarose gel electrophoresis and radiolabelled with ($[^{32}P]$dATP by random hexamer priming (Boerhinger Mannheim). The gene encoding CAI is expressed in BSC-1 cells. RNA extracted from growing, 1-, 2-, and 3-day quiescent BSC-1 cells is electrophoresed on a formaldehyde gel, transferred to a nylon membrane, and hybridized with the radiolabelled CAI probe. After expression of the CAI gene is detected, its time course is defined. RNA is obtained from cells at various stages of growth [day 1 after plating (log phase growth), day 6 after plating (confluent), day 9 after plating (quescent)], and Northern blots are prepared and hybridized with the CAI probe.

After the kinetics are determined, the effect of diverse cell stimuli on CAI gene expression is examined. The effect on CAI gene expression of exposure of BSC-1 cells to COM crystals is of particular interest. If exposure to crystals increases CAI expression, as it has other genes, then a protective feedback loop to defend cells against further crystal adhesion could be inferred. COM crystals (200 μg/ml) are added to 3-day quiescent BSC-1 cells and RNA is isolated between 1 and 24 hours later, as previously described. As controls, the effect of other urinary crystals (hydroxyapatite, brushite, uric acid) as well as latex beads is similarly determined. The effect of representative mitogenic stimuli on CAI gene expression is examined including 10% calf serum, EGF and ADP. The effect, if any, of these mitogenic signals on CAI gene expression is of particular interest because all three enhance COM crystal uptake, and a change in CAI transcription, translation, and secretion could represent part of a broad change in cellular responsiveness to crystals after exposure to exogenous signals. Changes in urinary excretion of specific molecules, such as calcium and oxalate, have been associated with an increased risk of stone formation. It is of interest, therefore, to determine if exposure of BSC-1 cells to increased concentrations of these molecules, as well as other agents that alter responsiveness of BSC-1 cells to COM crystals, modify CAI gene expression, perhaps as part of a protective response against crystal adhesion to cells. Cells are exposed to ADP (0–2 mM), calf serum (0.01%–10%), EGF (0–50 ng/ml), or increased calcium (1–10 mM/L) or oxalate (0.1–10 mM/L) concentrations for times between 1 and 48 hours, RNA is isolated, and Northern blots are prepared as described above.

Example 2
Use of CAI DNA Probes to Define the Distribution of CAI Gene Expression in Renal and Nonrenal Tissues After the sequence of the gene encoding CAI is available, the gene is used to study the tissue distribution of CAI gene expression. Since BSC-1 cells are derived from the African Green Monkey, it is likely that the gene encoding CAI in humans will be similar, and probes prepared from this sequence should be effective for study of human tissue.

Phage DNA obtained as disclosed herein is digested with the EcoR1 restriction enzyme, and the DNA sequence encoding CAI is isolated by agarose gel electrophoresis and radiolabelled with [$^{32}$P]dATP by random hexamer priming (Boerhinger Mannheim). A Multiple Tissue Northern Blot of human tissue (heart, brain, placenta, lung, liver, skeletal muscle, kidney, pancreas; Clonetech) is hybridized with the CAI probe.

The DNA and amino acid sequences of CAI are submitted to gene and peptide sequence databases. The identity of genes and/or proteins to which CAI is homologous, as well as the tissue distribution of CAI gene expression, provides important insights into potential physiologic role(s) for CAI in vivo, and whether the protein could function in nonrenal tissues as well.

Example 3
Use of the Two Monospecific Antibodies Prepared Against Peptide Fragments of CAI to Isolate Sufficient CAI to Study Its Physical-chemical Properties Two monospecific antibodies are available against synthetic peptides prepared from the sequence of the amino terminus and one internal fragment of CAI. These antibodies provide valuable reagents to construct antibody-affinity columns and prepare affinity-purified CAI for additional study.

The monospecific antibodies are coupled to CNBr-activated Sepharose 4B beads (Pharmacia) overnight at 4° C. in 0.2 M NaHCO$_3$, 0.5 M NaCl, pH 8.3; residual sites are blocked with 0.2 M glycine at pH 8.0 for 2 hours at room temperature. Antibody columns are prepared, equilibrated with 10 mM Tris, pH 7.5, and a solution of the antibody is diluted 1:10 in 10 mM Tris (pH 7.5) and passed over the column three times. The columns are washed with 10 mM Tris, pH 7.5, then 10 mM Tris, pH 7.5 plus 0.5 M NaCl, eluted with 100 mM glycine pH 2.5, followed by a wash of 10 mM Tris, pH 8.8 and then a second elution with 100 mM triethylamine, pH 11.5. Both acidic and basic elutions are tested for activity, and analyzed by SDS gel electrophoresis for a prominent band at $M_r$ 39,000 Da.

This procedure allows isolation of affinity-purified CAI. Because all anionic factors identified to date that block crystal adhesion to cells also block crystal growth, and CAI acts by coating crystals to block their adhesion to cells, it is likely that CAI will also block COM crystal growth. Quantitative assays of crystal growth established by Drs. Y. Nakagawa and F. Coe (Kidney Protein and Molecular Biology Center, University of Chicago) are used. The production of relatively large quantities of CAI also permits assays to evaluate its capacity to modulate adhesion of other urinary crystals (hydroxyapatite, uric acid) to the surface of renal cells. When sufficient quantities are available, CAI is submitted for carbohydrate analysis, and also for carbohydrate sequencing. (Kakehi and Honda, 1996; Paulus and Klockow, 1996) Since treatment with neuraminidase abolished anti-adhesion properties, it is likely that carbohydrate moieties contribute importantly to the biologic action of CAI. Large quantities of CAI permit study of the crystal structure of the molecule, and possible sites of its interaction with the crystalline surface of COM. The crystalline structure of CAI is also compared to that predicted by the amino acid sequence deduced from the full length gene.

Antibodies against synthetic peptide fragments of CAI may not recognize the native protein isolated from urine, or under specific assay conditions (ELISA, for example). If this is the case, immunoaffinity-purified CAI are prepared to immunize animals and to prepare additional polyclonal proteins against the intact, native protein. If sufficient immunoaffinity-purified native CAI is not available for immunization of rabbits, antigen is obtained from polyacrylamide gels as follows. Pooled fractions containing crystal adhesion inhibitory-activity from a Biogel sizing column are combined, concentrated and rinsed using a Centricon-30 microconcentrator and separated by SDS-PAGE. The gel is lightly stained with Coomassie blue (0.05% for 10 minutes), destained in water for 2 hours, and the predominant band at $M_r$ 39,000 excised. The gel slice is fragmented using two 5 ml syringes, combined with Freund's adjuvant, and injected subcutaneously into rabbits to produce polycolonal antibodies (Pocono Rabbit Farm and Laboratory, Inc.). Successful isolation of the gene encoding CAI also allows production of a fusion protein, which is useful as an antigen to prepare a polyclonal antibody in rabbits, if the antibodies raised against the synthetic peptide fragments do not detect native CAI under all conditions. Any polyclonal antibodies generated are analyzed for their ability to recognize CAI under different assay conditions (ELISA immunofluorescence, Western blots).

Example 4
Use of the Two Monospecific Antibodies Prepared Against Peptide Fragments of CAI to Screen the Urine of Normal Individuals and Patients with Nephrolithiasis to Detect CAI Renal epithelial cells in vivo release CAI into tubular fluid where it prevents adhesions of crystals to cells. CAI is an important defense against crystal retention in the kidney and eventual nephrolithiasis. Thus, patients who develop kidney stones might have reduced amounts or functionally abnormal CAI in their urine. Two monospecific antibodies available against the synthetic peptide fragments of CAI are used to screen the urine of normal humans and patients with nephrolithiasis for the presence of CAI.

Total protein in a 24-hour urine is isolated by dialysis and lyophilization (Porile, et al. 1996) and the amount of CAI in it is quantitated by direct ELISA as previously described utilizing the monospecific antibody that reacts most strongly against native CAI under these conditions. (Aithal et al. 1994) ELISA plate wells coated with dilutions of the antigen overnight at 4° C. and blocked with gelatin. Wells are incubated in succession with the primary antibody, avidin-linked secondary antibody, and CAI detected with an avidin-biotin-horseradish peroxidase system (Vector Labs, Burlinghame, Calif.). If the antibodies successfully detect CAI in normal human urine, the urine of patients with nephrolithiasis may also be screened. Patients with a wide range of known metabolic abnormalities such as idiopathic hypercalciuria, hypocitric aciduria, and hypouricosuria are useful for the screening. ELISA is used to determine if the quantity of CAI in the urine of stone formers is different in concentration and in the daily amount excreted compared to control individuals. Urine from specific patients is selected for analysis by Western blotting of total urinary protein to see if the antibodies detect CAI of an abnormal molecular size. If the electrophoretic mobility of CAI is abnormal by Western blotting, the immunoaffinity columns are utilized to isolate the dysfunctional CAI from urine. To initially characterize the CAI isoform, parameters that would be determined include carbohydrate content, amino acid composition, and 2-dimensional gel electrophoresis.

Antibodies against synthetic peptide fragments of CAI which lack carbohydrate may not recognize the native glycoprotein present in the urine in vivo. If this is the case, immunoaffinity purified or polyacrylamide gel-purified CAI are used to immunize rabbits to prepare a polyclonal antibody against the intact, native glycoprotein. This polyclonal antibody is analyzed for its ability to recognize CAI in urine. Alternatively, isolation of the gene encoding CAI allows production of a fusion protein, that is used to prepare a polyclonal antibody in rabbits. If the antibodies prepared against synthetic peptide fragments fail, it may be because CAI is heavily glycosylated and carbohydrate obstructs access of the antibody to the protein core.

Example 5
Utilizing the Two Monospecific Antibodies Prepared Against Peptide Fragments of CAI to Study the Tissue Distribution of CAI Protein Because two monospecific antibodies are available against synthetic peptides prepared from the sequence of the amino terminus and one internal fragment of CAI, they are used to determine the tissue distribution of CAI protein. These antibodies are used to screen normal human and rat tissue for the presence of CAI. Initially, a Multiple Tissue Western Blot (Clonetech) is probed with each affinity-purified antibody. As discussed herein, if hybridization is not detected, preparation of additional antibodies against immunoaffinity-purified CAI, polyacrylamide gel-purified CAI, and/or a fusion protein might be necessary. Sections of tissue from normal rats are screened for localization of CAI protein. Tissue blocks are fixed, mounted in paraffin, and sectioned in the EM-Cytomorphology Core Laboratory at the University of Chicago. Each of the monospecific antibodies against CAI serves as the primary antibody, and is detected with fluorescein-tagged anti-rabbit IgG. This antibody prepared against monkey CAI protein may not recognize rat CAI, and if this is the case a rat cDNA clone is isolated.

Example 6
Further Characterization of the Amino Acid Sequence of Peptide Fragments of the Crystal Adhesion Inhibitor (CAI) and the Nucleotide Sequences Encoding Some of the Internal Amino Acid Sequences A total of 261 amino acids have been identified of the estimated 355 amino acids of the Crystal Adhesion Inhibitor (CAI) molecule. Eleven of the amino acid sequences are listed in Table 4. These may include some sequences in FIG. 6. Three of the internal fragment sequences (8, 9, and 10 in Table 4) are linked by the sequence of the cDNA encoding the amino acid sequence underlined in Table 6. There are 149 nucleotides in the cDNA in Table 5.

The amino acid sequence formed by linking sequence 8, 9 and 10 in Table 4, can be linearized.

TABLE 4

Amino acid sequence of peptide fragments of Crystal Adhesion Inhibitor (CAI)[1]

Amino terminus: (K/D)INGGGATLPQPLYQTSGVLTAGFAPYI(S)V(N)(A)(K) (SEQ ID NO:4)
Internal fragments obtained after enzymatic digestions with Asp N protease
or Lys C protease:

1. (E)SKKFVVTTNFADSFGVPAGAVPAVTSQGVMD(S/A)(L)(N) (SEQ ID NO:5)
2. LIQVPSVATSVAIPFNK (SEQ ID NO: 6)
3. LAFLNNDYSQFGTGTKNVHWA (SEQ ID NO:7)
4. LTSTELSTYASTK (SEQ ID NO:8)
5. DQLPATGRTGNIVVVYRNEA (SEQ ID NO:9)
6. AA(P/F)TLA(G/H)LXAD (SEQ ID NO:10)
7. DNVSAAIAAVPVPAAANVALQNAYVVPVFA(D) (SEQ ID NO:11)
8. DPSVVPYPSTGYPILGTNLIFSQCYA (SEQ ID NO:12)
9. DATQTSQVRAFFTRRYGASALNT (SEQ ID NO:13)
10. DNAIKANRFVPLPTAWKAAITXNFVTATSAL (SEQ ID NO:14)

TABLE 5

Nucleotide sequence encoding the fragment of CAI underlined in bold in Table 6[1]

AACCTGATCTTCAGCCAGTGCTACGCCGACGCCACCCAAACCTCGCAAGTGCGTGCGTTCTTCACCCGTCACTAC
GGTGCCAGCGCCCTCAACACCAACGACAACGCCATCAAGGCCAACCGCTTTGTGCCGCTGCCAACTGCTTGGAA (SEQ ID NO:15)

TABLE 6

Three internal fragments of CAI (fragments #8, 9, 10 in Table4) linked by known nucleotide sequence 149 (underlined in bold)

DPSVVPYPSTGYPILGTNLIFSQCYADATQTSQVRAFFTRHYGASALNTNDNAIKANRFVPL
PTAWKAAITXNFVTATSAL (SEQ ID NO:16)

[1]X = unknown amino acid;
( ) = possible amino acid

MATERIALS AND METHODS

In Vitro Models of Crystal Adhesion

Cell Culture

Renal epithelial cells of the nontransformed African green monkey line (BSC-1) were used. Cells were grown in Dulbecco-Vogt modified Eagle's medium containing 25 mM glucose (DMEM), 1.6 μM biotin and 1% calf serum at 38° C. in a $CO_2$ incubator. Under these conditions, BSC-1 cells achieved confluence at $10^6$ cells per 60-mm plastic dish (Nunc). High-density, quiescent cultures were prepared by plating $2×10^6$ cells in a 60-mm dish. The spent medium was changed after 3 days so that there were $3–4×10^6$ cells/dish 6 days later. Medium was then aspirated and replaced with fresh medium containing 16 μM biotin and 0.01% calf serum; 3 days later the quiescent cultures were used for study.

Madin-Darby Canine Kidney (MDCK) cells were grown in DMEM containing 2% calf serum and 1.6 μM biotin as described previously. To prepare high-density, quiescent cultures $2×10^6$ cells/60-mm dish were plated in DMEM containing 2% calf serum and 1.6 μM biotin. The next day medium was aspirated and replaced with fresh medium containing 0.5% calf serum and biotin. One day later the cultures were used for study.

Balb/c3T3 fibroblasts were grown in DMEM containing 10% calf serum. To prepare high-density, quiescent cultures, $7×10^5$ cells were plated per 60-mm dish. Two days later the medium was aspirated and replaced with fresh medium containing 1% calf serum and 1.6 μM biotin; the cells were used one day later when a density of $17×10^6$ cells/dish was reached.

Subconfluent or high-density, quiescent cultures of renal epithelial cells of the nontransformed African green monkey line (BSC-1) or Madin-Darby canine kidney (MDCK) cells were employed. Crystals of COM (1–2 μm in size), both unlabelled and radiolabelled with [$^{14}$C] oxalic acid to a specific activity of 24,000 cpm/mg, were prepared as previously described (Lieske, 1993). Prior to use, crystals were sterilized by heating to 180° C. overnight, then suspended in distilled water to form a slurry from which they were added to the culture medium. X-ray crystallograptry, demonstrated that heating did not alter the structure of COM crystals.

Figure 3A:
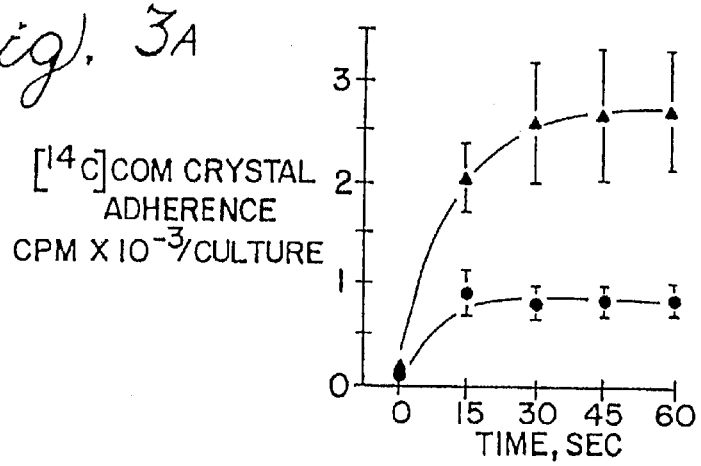
FIG. 3A illustrates time-dependence FIG. 3B concentration-dependence and FIG. 3C crystal-type specificity of COM crystal adhesion to BSC-I cells.
Figure 3B:
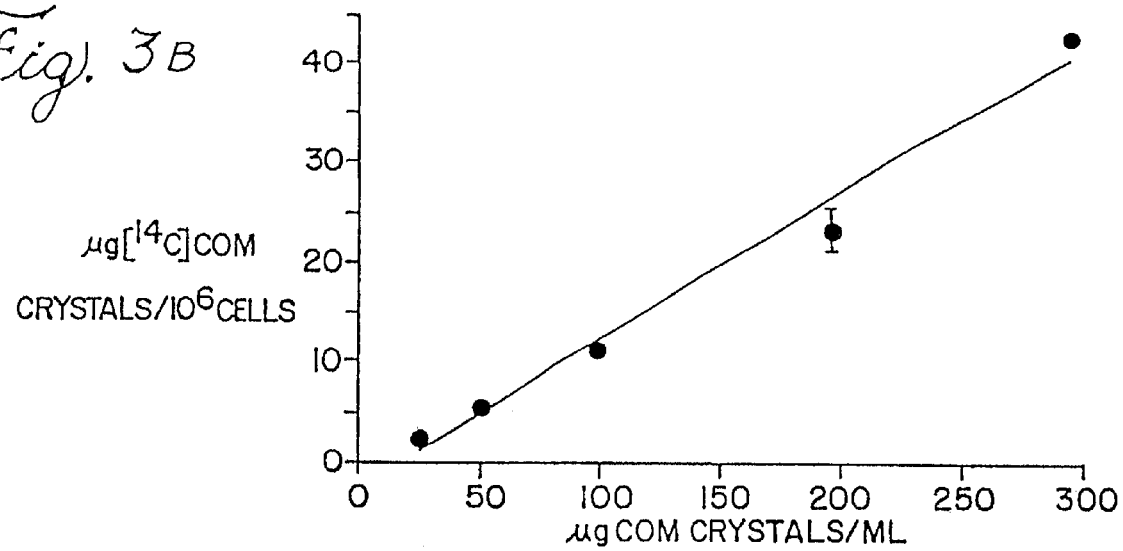

The interaction between renal epithelial cells (BSC-1 line) and the most common crystal in kidney stones, COM was studied in a tissue culture model system. COM crystals bound to the cell surface within seconds in a concentration-dependent manner to a far greater extent than did brushite, another calcium-containing crystal found in urine. In particular, initial adhesion of [$^{14}$C]COM crystals was maximal 15 seconds after 100 μg crystal/ml medium was added, and within 30 seconds when 300 μg/ml was used (FIG. 3A). Inspection by light microscopy showed that the presence of visible crystals correlated with cell-associated radioactivity. When measured one minute after addition, the quantity of adherent crystals increased linearly as a function of added crystal over the concentration range employed (12.5–300 μg/ml) (FIG. 3B). Thus, COM crystals can adhere within seconds to the surface of monkey or canine kidney epithelial cells in a concentration-dependent manner.

Figure 3C:
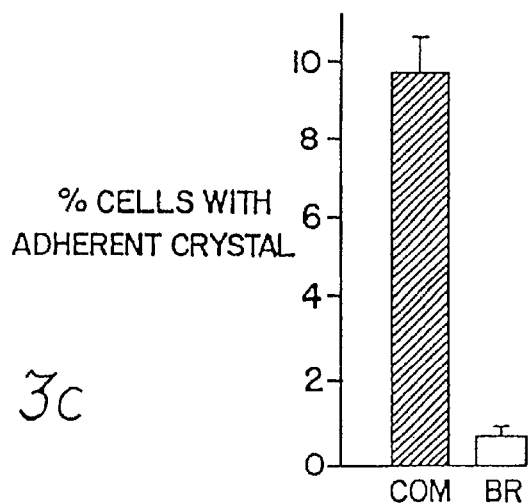

Addition of crystal amounts from 25 μg/ml (5.9 μg/cm2) to 300 μg/ml (70.8 μg/cm2 was associated with a linear increase in the quantity of bound crystal from 2.3±0.3 μg/$10^6$ cells to 43.2±1.0 μg/$10^6$ cells when measured after 2 minutes. As the concentration of added crystals was raised from 25 to 300 μg/ml, the amount adherent to confluent Balb/c3T3 fibroblasts increased linearly from 1.4±0.1 to 20.6±1.3 μg/$10^6$ cells. Binding of COM crystals 2 minutes after addition to confluent MDCK cells exhibited a similar linear concentration dependence. To confirm that cell-associated radioactivity represented adherent crystals, BSC-1 cells were examined under a microscope 2 minutes after addition of COM crystals (200 μg/ml). Inspection of 20 fields in 3 separate cultures revealed that 9.7±0.2% of cells had adherent crystals. In contrast, only 0.8±0.2% of cells were associated with BR (calcium phosphate) crystals (200 μg/ml) after 2 minutes (FIG. 3C).

Long-term Exposure of Cells to COM Crystals

To investigate the effect of crystal exposure for up to 15 days on renal epithelial cells, COM crystals (50 μg/ml) were added to near-confluent cultures of BSC-1 cells ($10^6$ cells/60-mm dish) containing 0.5% calf serum. Every four days thereafter the medium was aspirated and replaced with fresh medium containing 0.5% calf serum with no additional crystals. One, 8 and 15 days after addition of crystals, the medium was aspirated, and a solution of crystalline trypsin was used to detach the cells, which were then inspected under a microscope. The total number of cells in each culture was counted with a hemocytometer, and one hundred cells from each culture were scored for the presence of internalized crystals.

Effect of COM Crystals on Kidney Cell Structure

To study the cell-crystal interaction by transmission (TEM) or scanning (SEM) electron microscopy, high density cultures of BSC-1 cells were grown either on plastic 60-mm dishes (Permanox, Nunc) or on glass coverslips, respectively. Before and at specified times after addition of COM crystals (200 μg/ml) the medium was aspirated and cells were fixed with Karnofsky solution, and postfixed with osmium tetroxide as previously described. To optimally preserve intracellular architecture for TEM, pellets were prepared by scraping cells into an Eppendorf tube and collecting them by centrifugation at 3000 g prior to fixation. For TEM, the cells were fixed with Karnovsky solution (2% formaldehyde and 2.5% glutaraldehyde) in 0.2 M cacodylate buffer (pH 7.4) for 1 hour at 4° C., and postfixed in 2% osmium tetroxide in 0.2 M cacodylate buffer for 1 hour. Fixed cells were dehydrated in increasing concentrations of ethanol (35% to absolute) and embedded in Epon epoxy resin. Ultrathin sections were cut on a Sorvall MT2-B ultramicrotome, stained for one hour with uranyl acetate and for 3 minutes with lead citrate, and then examined at 80 kV with a Siemens 101 electron microscope. For SEM, cells fixed on glass coverslips were dehydrated in increasing concentrations of ethanol (10–100%). Each specimen was air dried, mounted on a stub, coated with gold for 4 minutes, and examined with an ETEC scanning electron microscope at 40 kV.

Cytoskeletal structures were examined by fluorescence microscopy in high density, quiescent cultures before and after exposure to COM crystals. At specified times after addition of COM crystals (100 µg/ml) the monolayer was rinsed with PBS and the cells were fixed with freshly prepared 0.037 M sodium phosphate buffer containing 0.01 M sodium periodate, 0.075 M lysine, and 2% paraformaldehyde for 15 minutes at room temperature. To stain F-actin, the coverslips were incubated with FITC-phalloidin (Sigma) for 20 minutes at room temperature in a humidified chamber, rinsed with PBS, and mounted. To visualize cytokeratin 8, cells fixed on coverslips were incubated for one hour with a specific anti-cytokeratin 8 monoclonal mouse IgG. Fluorescein-conjugated secondary antibody was added for one hour, and the coverslips were rinsed with PBS and mounted. After viewing under conventional immunofluorescence microscopy, fluorescence intensities on the coverslips stained for cytokeratin 8 were determined by acquisition of digitized video images, which were subsequently analyzed using Image 1 software (Universal Imaging).

Crystal Adhesion Assay for Candidate Inhibitors

Crystals of calcium oxalate monohydrate (COM) are prepared from supersaturated solutions as described Nakagawa, et al. (1981). To prepare radioactive COM crystals, [14C]oxalic acid (30–60 mCi/mmol, ICN Biomedicals, Irvine, Calif.) is added to a sodium oxalate solution to produce a specific activity of 105 cpm/ml, and sufficient calcium chloride is then added to form a supersaturated solution. The COM crystals that precipitate have a specific activity of 40,000–100,000 cpm/mg. Crystals are sterilized by heating to 180° C. overnight.

High-density, quiescent cultures of BSC-1 cells, MDCK cells, or Balb/c3T3 fibroblasts are prepared. At the time of assay, the medium is aspirated and replaced with 5 ml of phosphate-buffered saline (PBS) (10 mM Na2PO4, 155 mM NaCl, 5.4 mM KCl, pH 7.4 at 37° C.) to which the compound under investigation is added. [$^{14}$C]COM crystals are added to the buffer (200 µg/ml buffer; 47.2 µg/cm$^2$ of cells) from a sterile slurry in distilled water that is constantly stirred at 1500 revolutions/minute, as verified by a stroboscope, to prevent aggregation. The culture dishes are gently agitated for 5 seconds to uniformly distribute crystals which subsequently settle to the surface of the cell monolayer under the force of gravity. After two minutes buffer is aspirated and the cells are then washed three times with PBS (5 ml). The cell monolayer is then scraped directly into a scintillation vial containing 6 N HCl (0.5 ml) to which 4.5 ml of Ecoscint (National Diagnostics, E. Palmetto, Fla.) is added, and the amount of radioactivity is measured as described by Riese, et al. (1992).

In experiments to assess the effect of coating crystals with a specific candidate agent, [$^{14}$C]COM crystals are incubated in a solution of the compound of interest for 4 hours in an Eppendorf tube subjected to end-over-end rotation at room temperature. Each tube is then centrifuged at 3000 g for 5 minutes. The supernatant is gently aspirated and replaced with a supersaturated calcium oxalate solution to resuspend the coated crystals. To assure removal of any nonabsorbed compound, crystals are resuspended and washed three times in succession. Cell-associated radioactivity is determined 2 minutes after addition of these coated crystals as described herein.

In experiments to assess the effect of coating cells with a candidate agent, the medium of a three-day quiescent BSC-1 cell culture is aspirated and replaced with Hanks-buffered salt solution (HBSS) (137 mM NaCl, 5.4 mM KCl, 0.3 mM Na2HPO4, 0.4 mM KH2PO4, 4.2 mM NaHCO3, 1.3 mM CaCl$_2$, 0.5 mM MgCl$_2$, 0.5 mM MgCl$_2$, 0.5 mM MgCl$_2$, 5.6 mM glucose, pH 7.4 at 37° C.) to which a solution of the agent under study is added. Fifteen minutes later the buffer is aspirated from the culture dish and replaced with fresh HBSS; this procedure is repeated three times. Uncoated [$^{14}$C]COM crystals in water are then added to the cells to achieve a final concentration of 200 µg/ml medium. Radioactivity associated with the cells is measured 2 minutes later and compared to radioactivity of cultures to which CAI was added. Candidate agents that show the same or greater adhesion inhibiting than CAI, are considered for further testing, e.g., in animal models. Candidate agents that show less adhesion inhibition are generally not tested further except, for example, if the agents are believed to have other advantages.

Cellular Uptake of COM Crystals

At specified times after addition of crystals to high-density, quiescent cultures the medium was aspirated and a solution of crystalline trypsin was used to detach cells which were then inspected under a polarizing microscope. One hundred cells from each culture were counted, and each cell was scored for the presence of one or more internalized crystal(s).

Statistics

Data were compared by Student's t test; P values less than 0.05 were accepted as significant. Values presented are means±SEM. When no values for variances appear in the figures, it is because they are smaller than the symbol used for the mean.

Northern Blots

COM, HA, or BR crystals, or latex beads were each added to high-density, quiescent cultures to achieve a final concentration of 200 µg/ml (47.2 µg/cm$^2$). At specified times thereafter the medium was aspirated, cells were lysed in guanidinium isothiocyanate, scraped off the dish, and RNA was extracted. Samples of total RNA (20 µg each) were electrophoresed through a 1.4 agarose-6% formaldehyde gel, and transferred to a nylon membrane (Nytran, Schleicher & Schuell, Keene, N.H.). DNA probes were labeled with [α-$^{32}$P]dCTP by random hexamer priming, and hybridized to Northern blots at 42° C. in a solution containing 1 M NaCl, 1% sodium dodecylsulfate (SDS), 50% formamide, and 10% dextran sulfate. The blots were washed at 65° C. in 2×SSC buffer (0.3 M NaCl, 0.03 M Na citrate) containing 0.1% SDS. An autoradiogram of the blot was prepared at −70° C. for 24 to 72 hours using X-ray film and two intensifying screens.

The following DNA probes were purchased from the American Type Culture Collection (ATCC), Rockville, Md.: human acidic fibroblast growth factor (2.2 kb insert in pUC18); human collagenase (2.1 kb insert of pBR322); human gro (0.84 kb insert in pGEM-3); human heat shock protein (HSP)-70 (1.6 kb insert in pBluescript SK-); human interleukin-Iα (2.4 kb insert in pMG-5); human interleukin-1β (0.7 kb insert in pSM214); mouse interleukin-6 (5.2 kb insert in pBluescript SK+); rat stromelysin (1.7 kb insert from pUNI21); mouse tissue-type plasminogen activator (2.519 kb insert in pBluescript KS+), and human urokinase-type plasminogen activator (1.5 kb insert in pEMBL8). The following probes were obtained from laboratories at the University of Chicago: human c-sis (1.0 kb in pAM 18), human platelet-derived growth factor (PDGF)-A chain (1.3 kb insert in PUC 13), and human transforming growth factor TGF-β1 (1.0 kb NarI fragment of human TGF-β1) were from G. Bell; mouse Nur-77 (2.5 kb insert in pGEM4Z) was from L. DeGroot; rat glyceraldehyde-3-phosphate dehydrogenase (GAPDH) (1.2 kb insert in pBR322) was from M. Favus; mouse c-jun (2.6 kb insert in pGEM) was from D. Hallahan, and mouse EGR-1 (2.2 kb insert in pUCl3) from V. Sukhatme. The probe for rat fibronectin (0.27 kb StuI-EcoRI fragment in pGEM2) was obtained from R. Hynes (Massachusetts Institute of Technology, Cambridge, Mass.). Human c-myc (1.8 kb Eco RI fragment of the third exon of c-myc) was purchased from Oncor (Gaithersburg, Md.). Probes for mouse, βI-laminin (4.6 kb insert in pGEM 2) and mouse αIV-collagen (0.85 kb insert in pGEM2) were provided by Y. Yamada (NIH, Bethesda, Md.). Human plasminogen activator inhibitor (PAI-1) (2 kb insert in PAIB6) was obtained from D. Ginsburg (University of Michigan. Bovine basic fibroblast growth factor (4.2 kb insert in pGEM3Z) was obtained from R. Halaban (Yale University, New Haven, Conn.). Human c-fos probe (6.1 kb Ambrobe plasmid containing a 3.1 kb Xhol-Ncol fos gene fragment) was obtained from Amersham (Arlington Heights, Ill.). Human connective tissue growth factor (CTGF) (I.I kb in pRc/CMV) was provided by G. Grotendorst (University of Miami, Miami, Fla.). TGF-β2 cDNA was generated with the polymerase chain reaction using two nucleotide primers: one obtained from position 402 to 421 and the other primer spanning 969 to 988 of the full-length monkey cDNA sequence of TGF-β2.

CITED DOCUMENTS

Aithal, H. N., K. M. Knigge, S. Kartha, E. A. Czyzewski and F. G. Toback (1988). An alternate method utilizing small quantities of ligand for affinity purification of monospecific antibodies. *J. Immunol. Meth.* 112:63–70.

Aithal, H. N., M. M. Walsh-Reitz, S. Kartha, M. P. Janulis, T. E. Martin and F. G. Toback (1994). Glyceraldehyde-3-phosphate dehydrogenase modifier protein is associated with microtubules in kidney epithelial cells. *Am. J. Physiol.* 266: F612–F619.

Bitter, T., Muir, H. M. (1962). A modified uronic carbazole reaction. *Anal. Biochem.* 4:330–334.

Carey, D. J., Evans, D. M. (1989). Membrane anchoring of heparan sulfate proteoglycans by phosphatidylinositol and kinetics of peripheral and detergent-solubilized proteoglycans in Schwann cells. *J. Cell. Biol.* 108:1891–1897.

Fernandez, J., Andrews, L., Mische, S. M. (1994) An improved procedure for enzymatic digestion of polyvinylidene difluoride-bound proteins for internal sequence analysis. *Anal. Biochem.* 218:112–117.

Ginsberg, D., Zeheb, R., Yang, A. Y., Rafferty, U. M., Andreasen, P. A., Nielson, L., Dano, K., Lebo, R. V., Gelehrter (1986). cDNA cloning of human plasminogen activator-inhibitor from endothelial cells. *J. Clin. Invest* 78:1673–1680.

Grotendorst, G. R. (1 984). Alteration of the chemotactic response of NIH/3T3 cells to PDGF by growth factors, transformation, and tumor promoters. *Cell* 36:279–285.

Hess, B. (1992) Tamm-Horsfall glycoprotein—Inhibitor or promoter of calcium oxalate monohydrate crystallization processes. *Urol. Res.* 20:83–86.

Hess, B., Y. Nakagawa, and F. L. Coe (1989). Inhibition of calcium oxalate monohydrate crystal aggregation by urine proteins. *Am. J. Physiol.* 257:F99–106.

Kakehi, K, Honda, S. (1996) Analysis of glycoproteins, glycopeptides and glycoprotein-derived oligosaccharides by high-performance capillary electrophoresis. *J. Chromatog. A* 720:377–393.

Lieske, J. C., Swift, H. S., Martin, T., Patterson, B., Toback, F. G. (1994) Renal epithelial cells rapidly bind and internalize calcium oxalate monohydrate crystals. *Proc. Natl. Acad. Sci. USA* 91:6987–6991.

Lieske, J. C., Toback, F. G. (1993). Regulation of renal epithelial cell endocytosis of calcium oxalate monohydrate crystals. *Am. J. Physiol.* 264: F 800–F 807.

Lieske, J. C., M. M. Walsh-Reitz, and F. G. Toback (1992). Calcium oxalate monohydrate crystals are endocytosed by renal epithelial cells and induce proliferation. Am. J. Physiol. 262 (Renal *Fluid Electrolyte Physiol.* 31): F622–F630.

Lieske, J. C., B. Spargo, and F. G. Toback (1992). Endocytosis of calcium oxalate crystals and proliferation of renal tubular epithelial cells in a patient with type 1 primary hyperoxaluria. *J. Urol.* 148:1517–1519.

Linker, A., Hovingh, P. (1972). Heparinase and heparitinase from flavobacteria. *Meth. Enzymol.* 28:902–911.

Nakagawa, Y., V. Abram, F. J. Kezdy, E. T. Kaiser, and F. L. Coe (1983). Purification and characterization of the principal inhibitor of calcium oxalate monohydrate crystal growth in human urine. *J. Biol. Chem.* 258:12594–12600.

Nakagawa, Y., Margolis, H. C., Yokoyama, S., Kezdy, F. J., Kaiser, E. T., Coe, F. L. (1981). Purification and characterization of a calcium oxalate monohydrate crystal growth inhibitor from human kidney tissue culture medium. *J. Biol. Chem.* 256:3936–3944.

Paulus, A., Klockow A. (1996) Detection of carbohydrates in capillary electrophoresis. *J. Chromatog. A* 720:353–376.

Porile, J. L., Asplin, Jr., Parks, J. H., Nakagawa, Y., Coe, F. L.: Normal calcium oxalate crystal growth inhibition in severe calcium oxalate nephrolithiasis. *J. Am Soc Nephrol* 7:602–607, 1996.

Posnett, D. N., McGrath, H., Tam., J. P. (1988) A novel method for producing anti-peptide antibodies. *J. Biol. Chem.* 263:1719–1725.

Sukhatme, V. P., Kartha, S., Toback, F. G., Taub, R., Hoover, R. G., TsaiMorris, C. H. (1987). A novel early growth response gene rapidly induced by fibroblast, epithelial cell and lymphocyte mitogens. *Oncogene Res* 1:343–355.

Tartof, K. D., Hobbs, C. A. (1988) New cloning vectors and techniques for easy and rapid restriction mapping. *Gene* 67:169–182.

Toback, F. G. Induction of growth in kidney epithelial cells in culture by Na+ (1980). *Proc. Natl. Acad. Sci. USA* 77:6654–6656.

Vorbadt, A. W. (1989). Ultracytochemical characterization of anionic sites in the wall of brain capillaries. *J. Neurocytol.* 18:359–368.

Walsh-Reitz, M. M., and F. G. Toback (1983). Kidney epithelial cell growth is stimulated by lowering extracellular potassium concentration. *Am. J. Physiol.* 244 (*Cell Physiol.* 13):C429–C432.

Walsh-Reitz, M. M., Gluck, S. L., Waack, S., Toback, F. G. (1986). Lowering extracellular Na+ concentration releases autocrine growth factors from renal epithelial cells. *Proc. Natl. Acad. Sci. USA* 83:4764–4768.

Yamamata, T., Saito, H., Habuchi, O., Suzuki, S. (1968). Purification and properties of bacterial chondroitinases and chondrosulfatases. *J. Biol. Chem.* 243:1523–1535.

We claim:

1. A cDNA molecule comprising SEQ ID NO: 15.

* * * * *

SEQUENCE LISTING

<160> NUMBER OF SEQ ID NOS: 23

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Gly Asp Ser
 1

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ile Asn Gly Gly Gly Ala Thr Leu Pro Gln Pro Leu Tyr Gln Thr
 1               5                  10                  15

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Asn Asn Asp Tyr Ser Gln Phe Gly Thr Gly Thr Lys
 1               5                  10

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: K or D

<400> SEQUENCE: 4

Xaa Ile Asn Gly Gly Gly Ala Thr Leu Pro Gln Pro Leu Tyr Gln Thr
 1               5                  10                  15

Ser Gly Val Leu Thr Ala Gly Phe Ala Pro Tyr Ile Ser Val Asn Ala
                20                  25                  30

Lys

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (33)
<223> OTHER INFORMATION: S or A

<400> SEQUENCE: 5

Glu Ser Lys Lys Phe Val Val Thr Thr Asn Phe Ala Asp Ser Phe Gly
1               5                   10                  15

Val Pro Ala Gly Ala Val Pro Ala Val Thr Ser Gln Gly Val Met Asp
            20                  25                  30

Xaa Leu Asn
        35

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Ile Gln Val Pro Ser Val Ala Thr Ser Val Ala Ile Pro Phe Asn
1               5                   10                  15

Lys

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Ala Phe Leu Asn Asn Asp Tyr Ser Gln Phe Gly Thr Gly Thr Lys
1               5                   10                  15

Asn Val His Trp Ala
            20

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Thr Ser Thr Glu Leu Ser Thr Tyr Ala Ser Thr Lys
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Gln Leu Pro Ala Thr Gly Arg Thr Gly Asn Ile Val Val Val Tyr
1               5                   10                  15

Arg Asn Glu Ala
            20

<210> SEQ ID NO 10
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: P or F
<221> NAME/KEY: MOD_RES
<222> LOCATION: (7)
<223> OTHER INFORMATION: G or H
<221> NAME/KEY: MOD_RES
<222> LOCATION: (9)
<223> OTHER INFORMATION: unknown amino acid

<400> SEQUENCE: 10

Ala Ala Xaa Thr Leu Ala Xaa Leu Xaa Ala Asp
 1               5                  10

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Asn Val Ser Ala Ala Ile Ala Ala Val Pro Val Pro Ala Ala Ala
 1               5                  10                  15

Asn Val Ala Leu Gln Asn Ala Trp Val Pro Val Phe Ala Asp
            20                  25                  30

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Pro Ser Val Val Pro Tyr Pro Ser Thr Gly Tyr Pro Ile Leu Gly
 1               5                  10                  15

Thr Asn Leu Ile Phe Ser Gln Cys Tyr Ala
            20                  25

<210> SEQ ID NO 13
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Ala Thr Gln Thr Ser Gln Val Arg Ala Phe Phe Thr Arg His Tyr
 1               5                  10                  15

Gly Ala Ser Ala Leu Asn Thr
            20

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
```

```
<221> NAME/KEY: MOD_RES
<222> LOCATION: (22)
<223> OTHER INFORMATION: unknown amino acid

<400> SEQUENCE: 14

Asp Asn Ala Ile Lys Ala Asn Arg Phe Val Pro Leu Pro Thr Ala Trp
  1               5                  10                  15

Lys Ala Ala Ile Thr Xaa Asn Phe Val Thr Ala Thr Ser Ala Leu
             20                  25                  30

<210> SEQ ID NO 15
<211> LENGTH: 149
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
aacctgatct tcagccagtg ctacgccgac gccacccaaa cctcgcaagt gcgtgcgttc      60
ttcacccgtc actacggtgc cagcgccctc aacaccaacg acaacgccat caaggccaac     120
cgctttgtgc cgctgccaac tgcttggaa                                       149

<210> SEQ ID NO 16
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (72)
<223> OTHER INFORMATION: unknown amino acid

<400> SEQUENCE: 16

Asp Pro Ser Val Val Pro Tyr Pro Ser Thr Gly Tyr Pro Ile Leu Gly
  1               5                  10                  15

Thr Asn Leu Ile Phe Ser Gln Cys Tyr Ala Asp Ala Thr Gln Thr Ser
             20                  25                  30

Gln Val Arg Ala Phe Phe Thr Arg His Tyr Gly Ala Ser Ala Leu Asn
         35                  40                  45

Thr Asn Asp Asn Ala Ile Lys Ala Asn Arg Phe Val Pro Leu Pro Thr
     50                  55                  60

Ala Trp Lys Ala Ala Ile Thr Xaa Asn Phe Val Thr Ala Thr Ser Ala
 65                  70                  75                  80

Leu

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Ile Asn Gly Gly Gly Ala Thr Leu Pro Gln Pro Leu Tyr Gln Thr
  1               5                  10                  15

Ser Gly Val Leu
             20

<210> SEQ ID NO 18
```

```
<211> LENGTH: 20
<212> TYPE: PRT
<213> ORGANISM: Unknown Organism
<220> FEATURE:
<223> OTHER INFORMATION: Description of Unknown Organism: Comparison
      sequence

<400> SEQUENCE: 18

Asp Val Val Pro Gly Gly Ala Thr Leu Pro Gln Pro Leu Tyr Gln Thr
 1               5                  10                  15

Ala Gly Val Leu
            20

<210> SEQ ID NO 19
<211> LENGTH: 14
<212> TYPE: PRT
<213> ORGANISM: Unknown Organism
<220> FEATURE:
<223> OTHER INFORMATION: Description of Unknown Organism: Comparison
      sequence

<400> SEQUENCE: 19

Ala Val Val Gly Gly Gly Ala Thr Leu Pro Glu Lys Leu Tyr
 1               5                  10

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (29)
<223> OTHER INFORMATION: S or A

<400> SEQUENCE: 20

Phe Val Val Thr Thr Asn Phe Ala Asp Ser Phe Gly Val Pro Ala Gly
 1               5                  10                  15

Ala Val Pro Ala Val Thr Ser Gln Gly Val Met Asp Xaa Leu Asn
            20                  25                  30

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Ala Phe Leu Asn Asn Asp Tyr Ser Gln Phe Gly Thr Gly Thr Lys
 1               5                  10                  15

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ile Thr Ser Asn Phe Val Thr Ala Thr Ser Ala Leu
 1               5                  10

<210> SEQ ID NO 23
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (10)
<223> OTHER INFORMATION: unknown amino acid

<400> SEQUENCE: 23

Asn Arg Phe Val Pro Leu Pro Thr Ala Xaa Lys
 1               5                  10
```